United States Patent [19]

McAnalley

[11] Patent Number: 4,957,907

[45] Date of Patent: Sep. 18, 1990

[54] PROCESS FOR PREPARATION OF ALOE PRODUCTS

[75] Inventor: Bill H. McAnalley, Grand Prairie, Tex.

[73] Assignee: Carrington Laboratories Inc., Irving, Tex.

[21] Appl. No.: 301,986

[22] Filed: Jan. 25, 1989

Related U.S. Application Data

[63] Continuation of Ser. No. 144,872, Jan. 14, 1988, Pat. No. 4,851,224, which is a continuation-in-part of Ser. No. 869,261, Jun. 5, 1986, Pat. No. 4,735,935, which is a continuation-in-part of Ser. No. 810,025, Dec. 17, 1985, abandoned, which is a continuation-in-part of Ser. No. 754,859, Jul. 14, 1985, abandoned, which is a continuation-in-part of Ser. No. 750,321, Jun. 28, 1985, abandoned, which is a continuation-in-part of Ser. No. 649,967, Sep. 12, 1984, abandoned, which is a continuation of Ser. No. 375,720, May 7, 1982, abandoned.

[51] Int. Cl.$^5$ .................................................. A61K 31/715
[52] U.S. Cl. .................................... 514/54; 536/4.1; 536/123
[58] Field of Search .................. 424/195.1; 5.4/54; 536/4.1, 123

[56] References Cited

U.S. PATENT DOCUMENTS

| 145,062 | 12/1873 | Kappler | 424/195.1 |
|---|---|---|---|
| 149,262 | 3/1874 | Steelman | 424/195.1 |
| 150,129 | 4/1874 | Brewster | 424/195.1 |
| 153,683 | 8/1874 | Saalfeldt | 424/195.1 |
| 153,957 | 8/1874 | Hobson | 424/198.1 |
| 186,260 | 1/1877 | Margarit | 424/195.1 |
| 288,630 | 11/1883 | Green | 424/195.1 |
| 301,385 | 7/1884 | Mitchell | 424/195.1 |
| 327,847 | 10/1885 | Willis | 424/195.1 |
| 330,496 | 11/1885 | Kyte | 424/195.1 |
| 361,636 | 4/1887 | Laclaverie | 424/195.1 |
| 1,789,565 | 1/1931 | Sachs | 428/289 |
| 2,088,640 | 8/1937 | McIlvaine | 424/134 |
| 3,360,511 | 12/1967 | Fardas | 514/54 |
| 3,362,951 | 1/1968 | Farkas | 514/54 |
| 3,470,109 | 9/1969 | Marsh | 421/195.1 |
| 3,878,197 | 4/1975 | Maret | 424/195.1 |
| 3,892,853 | 7/1975 | Cobble | 424/195.1 |
| 3,920,816 | 11/1975 | Seegall | 424/195.1 |
| 3,973,008 | 8/1976 | Sugiyama et al. | 424/195.1 |
| 4,143,162 | 3/1979 | Tanaka | 426/89 |
| 4,178,372 | 12/1979 | Coats | 424/195.1 |
| 4,369,180 | 1/1983 | Mihalovits | 514/2 |
| 4,395,942 | 2/1983 | Thompson | 166/37 |
| 4,408,364 | 10/1983 | Thompson | 15/40 |
| 4,446,131 | 5/1984 | Maughan | 424/195.1 |
| 4,465,629 | 8/1984 | Maughan | 424/195.1 |
| 4,474,763 | 10/1984 | Lubowe | 514/2 |
| 4,481,185 | 11/1984 | Grollier et al. | 424/54 |
| 4,488,482 | 12/1984 | Cottrell | 180/37 |
| 4,500,510 | 2/1985 | Goldstein | 424/80 |
| 4,505,902 | 3/1985 | Millard | 424/195.1 |
| 4,555,987 | 12/1985 | Tamkinson | 100/118 |

FOREIGN PATENT DOCUMENTS

45589  3/1985  Japan .................................... 536/1.1

OTHER PUBLICATIONS

Chem. Abst. 87: 2889u, 1977.
Chem. Abst. 89: 103727, 1978.
Chem. Abst. 100: 35998s, 1984.
Brouse, "Aloe Vera Council Defends Its Practices, Product", FDA Consumer, pp. 29–30, Nov., 1981.
Crewe, "The External Use of Aloes", *Minnesota Medicine*, pp. 670–673, Oct., 1937.
Bogaard, "Report on the Analysis of 'Aloe Vera' Gel", Unisearch Ltd., Jul. 1985, pp. 1–3.
Goldemberg, Compounder's Corner: News and Views, *D&CI*, Jun. 1984, pp. 22.
Suga et al., "The Efficacy of the Aloe Plants Chemical Constituents and Biological Activities", *Cosmetics & Toiletries*, 98: 105 (1983).

(List continued on next page.)

*Primary Examiner*—John W. Rollins
*Attorney, Agent, or Firm*—Hubbard, Thurman, Turner, Tucker & Harris

[57] ABSTRACT

A process is described for extracting a pharmaceutically active polysaccharidic substance from the aloe plant.

The pharmaceutically active polysaccharidic substance and its characteristic properties are described.

11 Claims, 13 Drawing Sheets

OTHER PUBLICATIONS

Leung, "Aloe Vera Standards Should Be Meaningful", *D&CI*, Jan. 1983, pp. 39, 80.

De Navarre, "Desiderata: Aloe and Aloe", *Cosmetics & Toiletries*, 96: 12 (1981).

Gyanchandani, "Anthraquinone Drugs II: Inadvertent Acetylation of Aloe-Emodin During Preparation of Aglycones from Crude Drugs-UV, IR and NMR Spectra of the Products, *Journal of Pharmaceutical Sciences*, 58(7): 833-835 (1969).

McCarthy, "The Metabolism of Anthracene Derivatives and Organic Acids in Selected *Aloe* Species", *Plant Medica*, 16(3): 348-56 (1968).

Hirata, et al., "Biologically Active Constituents of Leaves and Roots of *Aloe arborescens* var. *natalensis*, *Z. Naturforsch*, 32c: 731-734 (1977).

Sapre, "Meiosis and Pollen Mitosis in *Aloe barbadensis* Mill., *Cytologia*, 40: 525-533 (1975).

Plenge, "Aloin", *Am. Jour. Pharm.*, Oct., 1884, pp. 507-508.

Gyanchandani et al., "Anthraquinone Drugs I: Thin-Layer Chromatographic Identification of Aloes, Cascara, Senna, and Certain Synthetic Laxatives in Pharmaceutical Dosage Forms", *Journal of Pharmaceutical Sciences*, 58(2): 197-200 (1969).

Varro E. Tyler et al., Pharmacognosy, pp. 60-63 (Lea & Febiger, Philadelphia 1981).

Arthur Osol et al., The U.S. Dispensatory and Physicians' Pharmacology, (J. B. Lippincott: Co., Philadelphia 1980) pp. 42-44.

Goodman & Gilman Eds. The Pharmacological Basis of Therapeutics, p. 984 (MacMillan Publishing Co., Inc. N.Y. 1975).

W. D. Winters et al., "Effects of Aloe Extracts on Human Normal and Tumor Cells In Vitro," Eco. Botany 35(1) at 89-95 (1981).

Ivan E. Danhof et al., "Stabilized Aloe Vera: Effect On Human Skin Cells," Drug and Cosmetic Ind. at 52-54, 105-106 (Aug. 1983).

David M. Morrow, M.D. et al., "Hypersensitivity to Aloe," Arch. Dermatol. 116 at 1064-1065 (9/80).

Melvin W. Green, "The Irritant Effect of Aloin Preliminary Note," Journal of the American Pharmaceutical Assn. 30, at 186-187 (1941).

E. R. Jansz et al., "The Aloin Content of Local Aloe Species," J. Nat'l. Sci. Coun. (Sri Lanka) 9(1) at 107-109 (1981).

F. R. Bharucha, "Effect of Prolonged Darkness on Acid Metabolism in the Leaves of Aloe Vera Linn," Sci. & Cult. 22 (7) at 389-390, (1/57).

Published report submitted to the National Aloe Science Council on or about 11/11/82 by the Southwest Institute for Natural Sources (Inc. by Ref.).

William F. Ganong, Review of Medical Physiology (Lange Medical Publications, Los Altos, CA) at 16-29, 984 (1983).

Mandal et al., "Structure of the Glucomannan Isolated from the Leaves of *Aloe Barbadensis* Miller," *Carbohydrate Research*, 87: 249-256 (1980).

Mandal et al., "Structure of the D-Galactan Isolated from *Aloe Barbadensis* Miller," *Carbohydrate Research*, 86: 247-257 (1980).

Mandal et al., "Characterisation of Polysaccharides of *Aloe Barbadensis* Miller: Part III-Structure of an Acidic Oligosaccharide" *Indian Journal of Chemistry*, 22B: 890-893 (1983).

Zimmerman, The Essential Guide to Nonprescription Drugs (Harper & Row, NY 1983).

James A. Duke, CRC Handbook of Medicinal Herbs, CRC Press, Inc. Boca Raton, Florida, p. 31, 1985.

R. Henry, Cosmetics and Toiletries, An Updated Review of Aloe Vera: Allured Publishing Corp., vol. 94, pp. 42-50, 1979.

Julia F. Morton, Folk Uses and Commercial Exploitation of Aloe Leaf Pulp: Economic Botany, vol. 15, pp. 311-316, 1961.

University of California, Berkeley Wellness Letter, "Myth: Aloe Can Heal A Variety of Ailments", Published in Association with the School of Public Health, 1(6): 8 (1985).

Leung, "Aloe Vera Update: A New Form Questions Integrity of Old", D&CI, Sep. 1985, pp. 42 and 44-46.

Leung, *Encyclopedia of Common Natural Ingredients Used in Food, Drugs and Cosmetics*, "Aloe (and Aloe Vera)" pp. 24-25 (date unknown).

Roboz et al., "A Mucilage From *Aloe Vera*", *Journal of the American Chemical Society*, 70: 3248-3249 (1948).

Yagi et al., "Aloe Mannan, Polysaccharide, from *Aloe Arborescens* var. *Natalensis*", Planta Med. 31(1): 17-20 (1977).

Haq et al., "Studies on Glucogalactomannan From the Leaves of *Aloe Vera*, Tourn. (Ex. Linn.)", *Bangladesh J. Sci. Inc. Res.*, 16: 68-72 (1981).

(List continued on next page.)

OTHER PUBLICATIONS

Marchessault et al., "Structural Studies On Triacetates of Mannan and Glucomannan", *Carbohydrate Polymers*, 1: 129–139 (1981).

Dea, "Specificity of Interactions Between Polysaccharide Helices and β1,4–Linked Polysaccharides", *American Chemical Society*, 439–454 (1981).

Gowda, "Structural Studies of Polysaccharides From *Aloe Saponaria* and Aloe Vanbalenii", *Carbohydrate Research*, 83: 402–405 (1980).

Shcherbukhin, et al., "Aggregation of Glucomannans in Aqueous Solutions", *Applied Biochemistry and Microbiology*, 15(6): 892–896 (1979).

Kuznetsov et al., "Native Glucomannans of Eremarus", *Dadledy Biochemistry Proceedings of the Academy of Sciences of the USSR*, 226(1): 214–216 (1976).

Rees et al., "Conformational Analysis of Polysaccharides: Stereochemical Significance of Different Linkage Positions in β–Linked Polysaccharides", *Chemical Communications*, 38: 1037–1038 (1969).

Matsuo et al., "Acetyl Groups in Native Glucomannan from Easter Lily Bulbs", *Agr. Biol. Chem.*, 38(2): 465–466 (1974).

Kato et al., "Studies on the Chemical Structure of Konjac Mannan Part I. Isolation and Characterization of Oligosaccharides from the Partial Acid Hydrolyzate of the Mannam", *Agr. Biol. Chem.*, 33(10): 1446–1453 (1969).

Segal et al., "A Reinvestigation of the Polysaccharide Material From *Aloe Vera* Mucilage", *Lloydia Proceedings*, 31(4): 423–424 (1968).

Orr, "Infra-red Spectroscopic Studies of Some Polysaccharides", *Biochimica Et Biophysica Acta*, 14: 173–181 (1954).

McKeown, "Aloe Vera: The Quest For the 'Curative' Missing Link", *Drug & Cosmetic Ind.*, 132: 30–32, 34–35 (1983).

Smothers, "Aloe Vera: The Importance of Processing", *Drug & Cosmetic Ind.*, 40, 77–80 (Jan. 1983).

"The History of Aloe Vera", Reference origin unknown. Duke et al., "Medicinal Plants of China" vol. 2, p. 396, Reference Publications, Inc. (1985).

Scarborough, Pharmacy in History: Roman Pharmacy and the Eastern Drug Trade, *American Institute of the History of Pharmacy* 24: 134–143 (1982).

Hutchens, *Indian Herbalogy of North America*, Merco, Ontario, Canada, pp. 8–10 (1981).

Spoerke, Jr., *Herbal Medications*, Woodbridge Press Publishing Company, Santa Barbara, CA, pp. 21–22, 185–186 (1981).

Gjerstad et al., "Current Status of Aloe As a Cure-All", *American Journal of Pharmacy*, 140: 58–64 (1968).

Hodge, "The Drug Aloes of Commerce, with Special Reference to the Cape Species", *Economic Botany*, 7: 99–129 (1953).

Goldberg, "The Aloe Vera Plant", *Archives of Dermatology and Syphilology*, 49: 46 (1944).

Tchou, "Aloe Vera (Jelly Leeks)", *Archives of Dermatology and Syphilology*, 47: 249 (1943).

Schoff, "Aloes", *American Oriental Society Journal*, 42: 171–185 (1922).

Fantus, "Aloes As a Medicine", *Journal of the American Pharmaceutical Association*, 11: 614–619 (1922).

Day, "The Botany of Aloes: The Aloe Plant", *The Journal of The American Pharmaceutical Association*, 11: 620–621 (1922).

Snow, "Pharmaceutical Preparations of Aloes", *The Journal of the American Pharmaceutical Association*, 11: 621–623 (1922).

Stuart, "Vegetable Kingdom: Aloe Vulgaris". *Chinese Materia Medica*, The American Presbyterian Mission Press, pp. 29–30 (1911).

Wilbert, "Commercial Aloes", *The American Journal of Pharmacy*, 75: 201–214, 264–273 (1903).

Barnes, "Physiological Section", *American Journal of Botany*, 34: 10, p. 597 (1947).

Bland, "Effect of Orally Consumed Aloe Vera Juice On Gastrointesinal Function in Normal Humans", *Preventive Medicine*, Linus Pauling Institute of Science & Medicine, Palo Alto, CA, Mar./Apr., 1985.

Kandil et al., "Protection of Gastric Mucosa By Aloe Vera, *J. Drug Res. Egypt*, 11, No. 1–2, pp. 191–196 (1979).

Blitz et al., "Aloe Vera Gel in Peptic Ulcer Therapy: Preliminary Report", *Journal of the American Osteopathic Association*, 62: 731–735 (1963).

United States Pharmacopedia Convention, Inc., "Compound Benzoin Tincture", *National Formulary*. USP 21, 17th Edition, pp. 99–100, 1985.

Saunders, Concanavilin: Dorland's Illustrated Medical Dictionary, 26th Edition, pp. 295 (1981).

Rubel, "Possible Mechanisms of the Healing Actions of (List continued on next page.)

OTHER PUBLICATIONS

Aloe Gel", *Botanicals in Cosmetics*, Terry Corporation, Melbourne, FL, vol. 98 (1983).

Fujita et al., "Bradykininase Activity of Aloe Extract", *Biochemical Pharmacology*, 25: 205 (1976).

Brasher et al., "The Effects of Prednisolone, Indonethacin, and *Aloe Vera* Gel on Tissue Culture Cells", *Oral Surgery, Oral Medicine, and Oral Pathology, 27: 122-128 (1969)*.

Robson et al., "Myth, Magic, Witchcraft, or Fact? *Aloe Vera Revisited*", *J. Burn Care Rehab.*, 3: 157-163 (1983).

Cera, et al., "The Therapeutic Efficacy of *Aloe Vera* Cream (Dermaide Aloe ®) in Thermal Injuries: Two Case Reports", *Journal of the American Animal Hospital Association*, 16: 768-772 (1980).

Ship, "Is Topical Aloe Vera Plant Mucus Helpful in Burn Treatment?", *JAMA*, 238: 1770 (1977).

Goff et al., "Measuring the Effects of Tropical Preparation Upon the Healing of Skin Wounds", *Journal of the Society of Cosmetic Chemists*, 15: 509-518 (1964).

Ashley, "The Use of Aloe Vera in the Treatment of Thermal and Irradiation Burns in Laboratory Animals and Humans", *Plastic and Reconstructive Surgery*, 20: 383-396 (1957).

Lushbaugh, et al., "Experimental Acute Radiciematitis Following Beta Irradiation V. Histopathological Study of the Mode of Action of Therapy with Aloe Vera", *Cancer*, 6: 690-698 (1958).

Rowe et al., "Further Observations on the Use of Aloe Vera Leaf in the Treatment of Third Degree X-Ray Reactions", *Journal of the American Pharmaceutical Association*, 30: 266-269 (1941).

Rowe, "Effect of Fresh Aloe Vera Jell in the Treatment of Third-Degree Roentgen Reactions on White Rats", *Journal of the American Pharmaceutical Association*, 29: 348-350 (1940).

Mandeville, "Aloe Vera in the Treatment of Radiation Ulcers of Mucous Membranes", *Radiology*, 32: 598-599 (1939).

Crewe, "Aloes in the Treatment of Burns and Scalds", *Minnesota Medicine*, 21: 538-539 (1939).

Loveman, "Leaf of Aloe Vera in Treatment of Roentgen Ray Ulcers", *Archives of Dermatology and Syphilology*, 36: 838-843 (1937).

Wright, "Aloe Vera in the Treatment of Roentgen Ulcers and Telangiectasis", *Jama*, 106: 1363-1364 (1936).

Collins et al., "Roentgen Dermatitis Treated with Fresh Whole Leaf of Aloe Vera", *American Journal of Roentgenology and Radium Therapy*, 33: 396-397 (1935).

Collins, "Alvagel as a Therapeutic Agent in the Treatment of Roentgen and Radium Burns", *The Radiological Review and Chicago Medical Recorder*, 57: 137-138 (1935).

Cock, "Aloes as a Local Sedative", *The British Medical Journal*, 2: 255 (1918).

Gjerstad, "Chemical Studies of Aloe Vera Juice—I: Amino Acid Analysis", *The University of Texas at Austin College of Pharmacy*, 28: 311-315 (1971).

Bouchey et al., "Chemical Studies of Aloe Vera Juice II: Inorganic Ingredients", *Quarterly Journal of Crude Drug Research*, 9: 1445-1454 (1969).

Report of the Joint Committee of the Pharmaceutical Society and the Society for Analytical Chemistry, "Recommended Methods for the Evaluation of Drugs: The Chemical Assay off Aloes", *Analyst*, 90: 593-596 (1965).

Fairbairn et al., "The Quantitative Conversion of Barbaloin to Aloe-Emodin and Its Application to the Evaluation of Aloes", *The Journal of Pharmacy and Pharmacology*, 15: 325-328 (1963).

Makino, et al., "Studies on the Constituents of Aloe Arborescens Mill. var. *natalensis* Berger. I. The Structure of Aloearbonaside, a Glucoside of a New Type Naturally Occurring Chromene", *Chem. Pharm. Bull.*, 21: 149-156 (1973).

Makino, et al., "Studies on the Constituents of Aloe Arborescens Mill. var. *natalensis* Berger II. The Structure of Two New Aloesin Esters", *Chem. Pharm. Bull.*, 22: 1565-1570 (1973).

Tilden, "Preliminary Notice of Some Products From Natal Aloes", *The Pharmaceutical Journal and Transactions*, Series 3, vol. 2: 951-952 (1872).

Bovik, "Aloe Vera: Panacea or Old Wives' Tale?", *Texas Dental Journal, 84: 13-16 (1966)*.

Zawahry, et al., "Use of Aloe in Treating Leg Ulcers and Dermatoses", *International Journal of Dermatology*, 12(1): 68-73 (1973).

Hegazy et al., "The Use of Aloe Vera Extract in the Treatment of Experimental Corneal Ulcers in Rabbit", *J. Drug. Res. Egypt*, 10 (1-2): 199-209 (1978).

Soeda, et al., "Studies on the Effect of Cape Aloe for Irradiation Leucopenia", 24: 1109-1110 (1964).

(List continued on next page.)

OTHER PUBLICATIONS

Jhaveri et al., "Clinical Evaluation of Infertility Associated with Irregular Menstrual Cycles Treated With an Indigenous Preparation", *Recent Advances in Human Reproduction*, Arthur Campos da Paz, et al., Eds., Exerpta Medica, 1976, pp. 61-65.

Barondes, "Lectins: Their Multiple Endogenous Cellular Functions", *Ann. Rev. Biochem.*, 50: 207-231 (1981).

Suzuki, et al., "Purification and Characterization of Two Lectrin from *Aloe arborescens Mill. J. Biochem.*, 85: 163-171 (1979).

Fujita, et al., "Specific Reaction of Aloe Extract with Serum Proteins of Various Animals", *Experientia*, 34: 523-524 (1978).

Gordon et al., "The Role of Concanavalin A Dissociation on Positive Cooperativity of Binding With Native and Fixed Erythrocytes", *The Journal of Biological Chemistry, 254(6): 1932-1937 (1978).*

Reeke, et al., "The Covalent and Three-Dimensional Structure of Concanavalin A", *The Journal of Biological Chemistry*, 150(4): 1525-1547 (1975).

Agrawal, et al., "Protein-Carbohydrate Interaction, IVIII, The Preparation and Properties of Acetylated Concanavalin A, the Hemogglutinin of the Jack Bean", *Biochemistry*, 7(12): 4211-4218 (1968).

Sharon, "Lectins", *Scientific American*, 236: 108-119 (1977).

Northway, "Experimental Use of Aloe Vera Extract in Clinical Practice", *Veterinary Medicine/Small Animal Clinician*, Jan. 1975, pp. 89.

Clinical Data, "The Local Action of Aloes on Regeneration", *Journal of the American Veterinary Medical Association*, 99: 296 (1941).

McLaughlin, "Roentgen Ray Dermatitis Treated with Ointment Containing Viosterol", *Archives of Dermatology and Syphilology*, 34: 901-903 (1936).

Flagg, "Aloe Vera Gel in Dermatological Preparations", *American Perfumes and Aromatics*, 74: 27-28, 61 (1959).

Fine, "Cultivation and Clinical Application of Aloe Vera Leaf", *Radiology*, 31: 735-736 (1938).

Hamilton, "Acute Vesicular Dermatitis Caused By Ciracao Aloes", *The Medical Journal of Australia*, 1: 302-303 (1932).

Anderson, "Aloe Vera Juice: A Veterinary Medicament?", *The Compendium on Continuing Education for the Practicing Veterinarian, 5: 364-368 (1983).*

Grieve, "Aloes", *A Modern Herbal*, vol. I., Dover Publications, Inc. New York, 1971, pp. 26-29.

Ivy, et al. (I), "The Effect of Aloes and Podophyllum (Resin) (Carter's Little Liver Pills) on the Output of Bilirubin and Cholic Acid in Duodenal Drainage in "Constipated" Human Subjects", *Quarterly Bulletin, Northwestern University Medical School*, 19: 189-193 (1945).

Ivy, et al. (II), "Do Aloes and Podophyllum (Carter'-Little Liver Pills) Increase the Flow of Bile Into the Duodenum?", *Gastroenterology*, 5: 27-33 (1945).

Hazleton, "The Influence of Aloe and Podophyllum on the Flow of Hepatic Bile in the Dog.", *Journal of the American Pharmaceutical Association*, 31,: 53-56 (1942).

Ivy et al., (III), "The Effect of Aloes and Podophyllum and Carter's Little Liver Pills on Bile Formation", *Quarterly Bulletin, Northwestern University Medical School*, 16: 197-102 (1942).

Viehoever, "Evaluation of Aloe", *Am. Jour. Pharm.*, 107:47-72(1935).

Munch, *Bioassays: A Handbook of Quantitative Pharmacology*, The Williams and Wilkins Company, Baltimore, 1931, pp. 769-781.

Gathercoal et al., "What is Aloes, U.S.P.?", *Journal of the American Pharmaceutical Association, 11: 523-526 (1922).*

Day et al., "Botany of Aloes", "Pharmacognosy of Aloes", "Therapeutics of Aloes", and "Preparations of Aloes", *Journal of the American Pharmaceutical Association*, 11: 462-463 (1922).

Nosokomos, "On the Use and Abuse of Aloes", *London Medical Gazette*, 4: 139-143 (1829).

Meadows, "Formulating Cosmetics with Aloe Vera", *Drug & Cosmetic Ind.*, 132: 36-40 (1983).

Noll, "Today's and Tomorrow's Cosmetics with Aloe Vera Gel", *Journal of the Society of Cosmetic Chemists*, 34: 174-175 (1983).

Moroni, "Aloe in Cosmetic Formulations", *Cosmetic Technology*, Sep. 1982, pp. 40-45.

Schoen, "Aloe Vera Cosmetics", *The AMA Book of Skin and Hair Care*, J. B. Lippincott Company, New York, 1977, pp. 41-42.

Leung, "Aloe Vera in Cosmetics", *Drug & Cosmetic Ind.*, 1977, pp. 34-35, 154-155.

Hoffenberg, "*Aloe vera* An Old Herbal Medica- (List continued on next page.)

OTHER PUBLICATIONS tion–New In Cosmetics", *Soaps–Oils–Fats–Waxes, 17*: 499–502 (1979).

Trachtenberg, "Cytochemical and Morphological Evidence for the Involvement of the Plasma Membrane and Plastids in Mucilage Secretion in *Aloe Arborescens*", *Annals of Botany*, 53; 227–236 (1984).

Vij et al., "Cytogenetical Investigations into Some Garden Ornamentals II. The Genus *Aloe L.*", *Cytologia*, 45: 515–532 (1980).

Abraham et al., "Occurrence of Triploidy in *Aloe vera* Tourn. ex Linn.", *Current Science*, 48: 1001–1003 (1979).

Bartakke et al., "Crassulacean Acid Metabolism and Photosynthesis in *Aloe Barbadensis* Mill", *Photobiology*, 42B (4&5):227–233 (1976).

Lu et al., "Lateral Thickening in the Stem of *Agave Rigida* Mill", and *Aloe Vera L., Taiwania*, 21(2): 204–219 (1976).

Groenewald, et al., "*Callus Formation* and Plant Regeneration From Seed Tissue of *Aloe Pretoriensis* Pole Evans", *Z. Pflanzenphysiol. Bd.* 75, S, 270–272 (1975).

Gupta et al., "Chromosomal Aberrations Induced by Maleic Hydrazide in *Aloe Vera*", *Acta Botanica Academiae Scientiarum Hungaricae*, 17: 51–58 (1971).

Gunther, "The Greek Herbal of Dioscorides", Hafner Publishing Company, New York, 1968, pp. 257–258.

Vig, "Spontaneous Chromosome Abnormalities in Roots and Pollen Mother Cells in *Aloe Vera L.*", *Bulletin of the Torrey Botanical Club*, 95(3): 254–261 (1968).

Vyas, "Staminal Abnormalities in *Aloe Vera* Linn.", *Science and Culture*, 30: 145–146 (1964).

Rowe et al., "A Phytochemical Study of *Aloe Vera* Leaf", *Journal of the American Pharmaceutical Association*, 30: 262–265 (1941).

Marshak, "*Chromosomes and Compatibility in the Aloinae*", *American Journal of Botany*, 21(9): 592–597 (1934).

Holdsworth, "Chromones in Aloe Species", Department of Chemistry, University of Papua and New Guinea, pp. 322–325.

Excerpt from Brochure of Dr. Madis Laboratories, Inc., South Hackensack, NJ, "Veragel".

Waller et al., "A Chemical Investigation of *Aloe Barbadensis* Miller", *Proc. Okla. Acad. Sci.* 58: 69–76 (1978).

Rauwald et al., "7-Hydroxyaloin: the Leading Substance from Aloe Barbadensis in Ph. Eur. III", *Arch. Pharm. (Weinheim)*, 315: 477–478 (1982).

Rauwald, "Preparative Separation of the Diastereomeric Aloins by Droplet Counter–Current Chromatography", *Arch. Pharm. (Weinheim)*, 315: 769–772 (1982).

Yagi, et al., "Effect of Aloe Lectin on Deoxyribonucleic Acid Synthesis in Baby Hamster Kidney Cells", *Experientia*, 41: 669–671 (1985).

*Physiological Effects of Food Carbohydrates*, Jeanes et al., Ed., American Chemical Society, Washington, DC 1975, pp. 296–311.

Flesch, "Mucopolysaccharides in Human Epidermis," *Journal of the Society of Cosmetic Chemists*, 10(1): 154–158 (1959).

Gorin, "Assignment of Signals of the Carbon—13 Magnetic Resonance Spectrum of a Selected Polysaccharide: Comments on Methodology", *Carbohydrate Research*, 39: 3–10 (1975).

Bible, *Interpretation of NMR Spectra An Empirical Approach*, Plenum Press, New York, 1965, pp. 7–48.

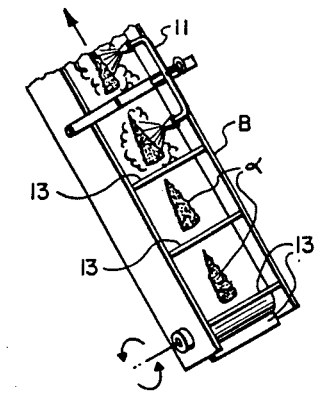
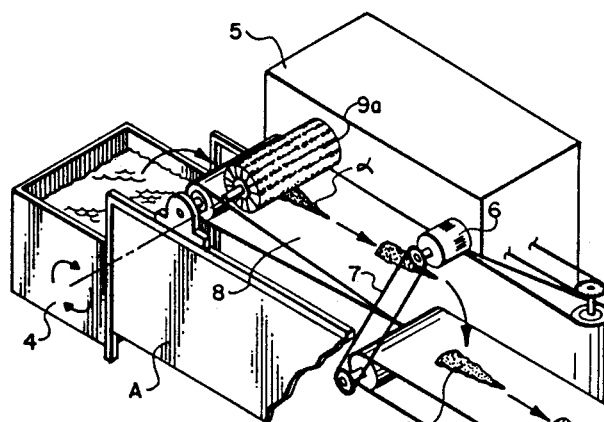
FIG. 3B
FIG. 3A
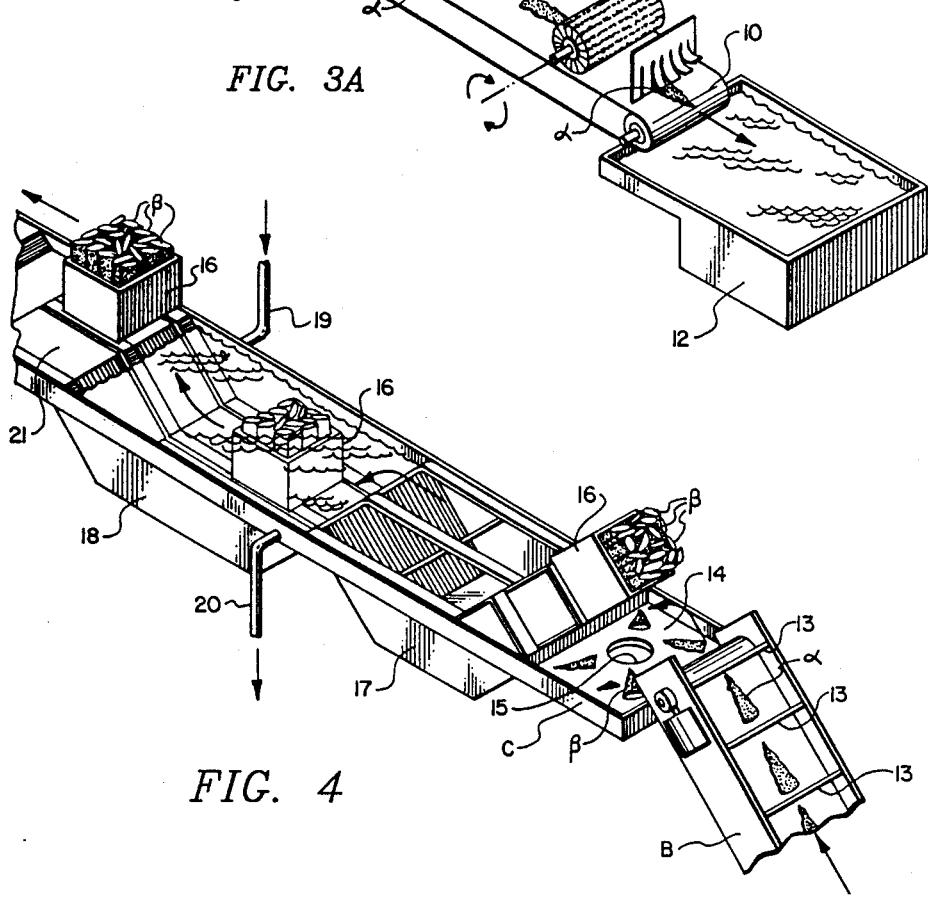
FIG. 4

PROCESS FOR PREPARATION OF ALOE PRODUCTS

RELATED APPLICATIONS

This is a continuation-in-part of U.S. application Ser. No. 869,261, now U.S. Pat. No. 4,735,935, the entire contents and disclosure of which are hereby specifically incorporated by reference. Said U.S. application Ser. No. 869,261 corresponds to International Application No. PCT/US86/01335, filed June 20, 1986 and published under International Publication No. WO 87/00052 on Jan. 15, 1987, the entire contents and disclosure of which are also hereby specifically incorporated by reference. Said U.S. application Ser. No. 869,261 is a continuation-in-part of a U.S. application Ser. No. 810,025, filed Dec. 17, 1985 (now abandoned), which was a continuation-in-part of U.S. application Ser. No. 754,859, filed July 12, 1985 (now abandoned), which was a continuation-in-part of U.S. application Ser. No. 750,321, filed June 28, 1985 (now abandoned), which was a continuation-in-part of U.S. application Ser. No. 649,967, filed Sept. 12, 1984 (now abandoned), which was a continuation of U.S. application Ser. No. 375,720, filed May 7, 1982 (now abandoned). Said application Ser. No. 869,261 being entitled "Processes for Preparation of Aloe Products, Products Produced Thereby and Compositions Thereof". Said applications Serial Nos. 754,859; 649,967; and 375,720 being entitled "Process for Preparation of Aloe Vera Products".

BACKGROUND OF THE INVENTION

1. Field of the Invention

This invention pertains to the field of processing aloe plants and removing portions of said plant for processing same into compositions for topical and internal applications, and compositions of matter comprising said portions of aloe.

2. Description of the Prior Art, and Other Information

Aloe vera is not a cactus plant, as widely believed, but rather a member of the lily family. Aloe is a tropical or subtropical plant characterized by lance-shaped leaves with jagged edges and sharp points There are about 360 species of aloe plants known. Harding, *Aloes of the World: A Checklist, Index and Code*, Excelsa 9: 57-94 (1979). They seem to thrive in hot, arid areas and are widely scattered from the Mediterranean Sea, Middle East, Africa, China, Japan, Mexico and the southern U.S.A. A few of the important species used for their medicinal properties are *Aloe barbadensis* Miller (aloe vera), *A. arborescens, A. plicatilis, A. vahombe, A. saponaria, A. africana, A. ferox* and *Aloe perryi*. Reynolds, *Aloes of Tropical Africa and Madagascar*, The Trustees, The Aloe Book Fund, Mbabane Swaziland. However, *A. barbadensis* Miller is generally recognized as the "true aloe" because of its wide use and, reportedly, most effective healing power, although in Japan, *A. arborescenes* Miller traditionally has been used as a folk remedy for various ailments ranging from gastrointestinal disorders to athlete's foot.

Aloe vera is a perennial plant with turgid green leaves joined at the stem in a rosette pattern. The leaves of a mature plant may be more than 25 inches long with saw-like spikes along their margins.

Slicing the leaf transeversely as shown in FIGS. 1 and 2 reveals the outer walls of the epidermis 3 covered with thick cuticles. Beneath the epidermis 3 is the mesophyll which is differentiated into chlorenchyma cells and thinner walled cells known as parenchyma. The parenchyma cells harbor a transparent mucilaginous jelly 1. The vascular bundles 2 with inner bundle sheath cells contain the yellow sap having laxative properties and are sandwiched between the two major cells Needle shaped crystals of calcium oxalate, produced as a metabolic byproduct in plant cells, are found mostly at the central portion of the leaf.

Aloe vera contains two major liquid sources, a yellow latex (exudate) and the clear gel (mucilage). The dried exudate of *Aloe barbadensis* Miller leaves is referred to aloe. The commercial name is Curacao aloe. It is composed mainly of aloin, aloe-emodin and phenols. Bruce, *South African Medical Journal*, 41: 984 (1967); Morrow et al., *Archives of Dermatology*, 116: 1064-1065 (1980); Salek et al., *Corrosion Prevention & Control*, 9-10 (1983); Mapp et al., *Planta Medica*, 18: 361-365 (1970); Ranwald, *Archives Pharmazie*, 315: 477-478 (1982). A number of phenolics, including anthraquinones and their glycosides, are known to be pharmaceutically active. Bruce, *Excelsa* 5: 57-68 (1975); Suga et al., *Cosmetics and Toiletries*, 98: 105-108 (1983).

The mucilaginous jelly from the parenchymal cells of the plant is referred to as Aloe vera gel. There are generally no anthraquinones to decompose and cause discoloration of the gel unless the gel is contaminated by an improper processing technique.

Aloe vera gel is about 98.5% water by weight. More than 60% of the total solid is made up of polysaccharides of carbohydrate origin. Organic acids and inorganic compounds, especially calcium oxalate, account for the remainder of the solid.

Whole leaves, exudates and fresh gels of Aloe plants have been used for a variety of human afflictions. Evidence of their use as a medicinal remedy can be traced to the Egyptians of 400 BC. Aloe vera was also used to embalm the dead, as well as to protect the embalmers from the death-causing agent. Other early civilizations used aloe vera for skin care, to relieve insect stings and bites, to treat scratches and ulcerated skin, to promote wound healing, to prevent hair loss and as a purgative. It was the traditional medicine of many cultures as an anthelmintic, cathartic and stomachic and was used inter alia for leprosy, burns and allergic conditions. Cole et al., *Archives of Dermatology and Syphilology*, 47: 250 (1943); Chopra et al., *Glossary of Indian Medicinal Plants*, Council of Scientific and Industrial Research, New Delhi; Ship, *Journal of the American Medical Association*, 238: 1770-1772 (1977); Morton, *Atlas of Medicinal Plants of Middle American Bahamas to Yucatan*, Charles C. Thomas Publisher, 78-80 (1981); Diez-Martinez, La Zabila, Communicado No. 46 *Sobre Recursos Bioticos Potenciales del Pais*, INIREB, Mexico (1981); Dastur, *Medicinal Plants of India and Pakistan;* D. B. Taraporevala Sons & Co., Private Ltd., Bombay 16-17 (1962).

Aloe vera has enjoyed a long history of lay acceptance as possessing "curative" or "healing" qualities. Over the last few years, numerous books and articles meeting scientific standards have been written on Aloe vera. Organizations such as the Aloe Vera Council and recognized medical institutions, through publications and case-histories of physicians, veterinarians and other scientists, have given credence to the "aloe phenomenon". Aloe vera has been featured extensively in the field of dermatology, especially for treating radiation-caused skin conditions. Mackee, *X-Rays and Radium in the Treatment of Diseases of the Skin*, 3rd Ed., Lea and Febiger, Philadelphia, 319-320 (1938); Rovalti et al., *Industrial Medicine and Surgery*, 28: 364-368 (1959); Zawahry et al., *Quotations From Medical Journals on Aloe Research*, Ed. Max B. Skousen, Aloe Vera Research Institute, Cypress, Calif., 18-23 (1977); Cera et al., *Journal of the American Animal Hospital Association*, 18: 633-638 (1982). The body of scientific literature documenting medical applications in digestive problems, as a virucidal, bactericidal and fungicidal agent and in gynecological conditions is extensive and has been adequately reviewed by Grindlay and Reynolds (*Journal of Ethnopharmacology*, 16: 117-151 (1986)).

The importance of chemicals found in aloes is indicated by the fact that they have been listed in every known national pharmacopeia. *U.S. Pharmacopeia*, 20th Revision, The National Formulary, 14th Edition, United States Pharmacopeial Convention, Inc., Rockville, Md., July 1, 1980. However, the U.S. Pharmacopeia describes the yellow sap drug portion of aloes but not the mucilage. The fresh unpreserved gel is about 98.5-99.2% water. The total solid that remains after the water has been removed ranges from 0.8 to 1.5%. The mucilage, sugars, fiber, proteins, ash, fats, aloin and resin are the major constituents of the solid. Robson et al., *Journal of Burn Care Rehabilitation*, 3: 157-163 (1982). Compositions that include enzymes, organic acids, inorganic salts, amino acids and alkaloids have been noted. Rowe et al., *Journal of the American Pharmaceutical Association*, 30: 262-266 (1941); Roboz et al., *Journal of the American Chemical Society*, 70: 3248-3249 (1948); Waller et al., *Proceedings of Oklahoma Academy of Science*, 58: 69-76 (1978). Depending on the way in which the leaves are processed, mucilage and sugars are the major components of the dehydrated gel. The sugars found are galactose, glucose, mannose, rhamnose, xylose and uronic acids. Although conflicting reports have been observed, the mucilage is mainly composed of mannan or glucomannan. Eberendu et al., *The Chemical Characterization of Carrisyn TM* (in preparation); Mandal et al., *Carbohydrate Research*, 87: 249-256 (1980b); Roboz et al., *Journal of the American Chemical Society*, 70: 3248-3249 (1948); Gowda et al., *Carbohydrate Research*, 72: 201-205 (1979); Segal et al., *Lloydia*, 31: 423 (1968).

Presently, the controversy over the identity of the active substance(s) in aloe vera has not been settled. It is therefore, important to clearly distinguish between the components present in the gel and those found in the exudates A larger part of the gel is a mucilage of mainly polysaccharide nature with minor amounts of various other compounds. It is conceivable that there may be some synergistic action between the polysaccharide base and other components in some of the activities observed. Leung, *Excelsa* 8: 65-68 (1978); Henry, *Cosmetics and Toiletries*, 94: 42-50 (1979). For example, several workers report that the effective components for wound healing may be traumatic acid (Freytag, *Pharmazie*, 9: 705 (1954)) and a kind of polysaccharide. Kawashima et al., *Chemical Abstracts*, 93: 13075 (1979). Mackee, supra, noted that the gel, not the rind or the exudate, was responsible for the beneficial effects in the treatment of radiation burns, and he stressed the importance of using fresh leaves for effective treatment. Polysaccharides degrade with time and certain molecular weight sizes may be necessary to elicit specified pharmacological response. Goto et al., *Gann*, 63: 371-374 (1972).

There are many examples in the literature that polysaccharides can exhibit pharmacological and physiological activities without help from other components. G. Gialdroni-Grassi, *International Archives of Allergy and Applied Immunology*, 76 (Suppl. (1): 119-127 (1985); Ohno et al., *Chemical and Pharmaceutical Bulletin*, 33: 2564-2568 (1985); Leibovici et al., *Chemico-Biological Interactions*, 60: 191-200 (1986); Ukai et al., *Chemical and Pharmaceutical Bulletin*, 31: 741-744 (1983); Leibovici et al., *Anticancer Research*, 5: 553-558 (1985). One such example relates to development of atherosclerosis. Hyperlipidemia in the general population and especially in familial hypercholesterolemia is associated with coronary heart disease and death. In countries where dietary fiber intake is high, atherosclerosis appears to be uncommon. Trowell et al., Editors, *Refined Carbohydrate Foods and Disease*, London, Academic Press, 207 (1975). Pectin and guar are reported to lower cholesterol in normal and hyperlipidemic patients. Kay et al., *American Journal of Clinical Nutrition*, 30: 171-175 (1977). Locust bean gum, a polysaccharide composed of mannose and galactose, decreased the plasma lipoprotein cholesterol concentrations in both normal and familial hypercholesterolemic subjects. Zavoral et al., *American Journal of Clinical Nutrition*, 38: 285-294 (1983). Addition of guar gum to carbohydrate meals decreased the postprandial rise of glucose in both normal and diabetic subjects. Jenkins et al., *Lancet*, 2: 779-780 (1977). Kuhl et al., (*Diabetes Care*, 6 (2): 152-154 (1983)) demonstrated that guar gum exhibited glycemic control of pregnant insulin-dependent diabetic patients.

The anti-tumor activity of polysaccharides has been widely reported. Polysaccharides prepared from *Lentinus cyathiformis* are known to increase hosts' defense against tumors Rethy et al., *Annales Immunologiae Hungaricae*, 21: 285-290 (1981). There are several reports that polysaccharides from mushroom, yeast or bacterial extracts can elicit a high degree of host defense activity against viral and tumor infestations. Chihara et al., *Nature*, 222: 687 (1969); Schwartzman, *Proceedings of the Society for Experimental Biology and Medicine*, 29: 737 (1932); Rethy, *X. International Congress of Microbiology*; Moscow, 642 (1966) Suzuki et al. (*Journal of Pharmacobio-Dynamics*, 7: 492-500 (1984) also reported anti-tumor activity of a polysaccharide fraction (GF-1) extracted from cultured fruiting bodies of a fungus, *Grifola frondosa*. This fraction showed equivalent, high levels of inhibiting activity when administered intraperitoneally (IP), intravenously (IV) and intratumorally (IT). However, oral administration (PO) was not effective. The GF-1 fraction also exhibited anti-tumor action against the solid form of Meth A fibrosarcoma and MM 46 carcinoma in mice. Lentinan, which is a 6-branched $\beta$-1-3-linked glucan similar to GF-1, was ineffective against Meth A fibrosarcoma. Chihara, The antitumor polysaccharide Lentinan an overview; "Manipulation of Host Defense Mechanisms"; ed. by Aoki et al., *Excerpta Medica*, North Holland, 1-16 (1981); Sasaki et al., *Carbohydrate Research*, 47: 99-104 (1976). Synthesized branched polysaccharides were reported to demonstrate activities against tumors. Matsuzaki et al., *Makromol. Chem.*, 186: 449 (1985). Matsuzaki et al. (*Makromol. Chem.*, 187: 325-331 (1986)) synthesized branched polysaccharides, which showed significant activities, from ivory nut mannan ($\beta$-(1→4)-D-mannopyranose) and β-(1→4)-linked glucomannan. A partially acetylated linear β-(1→3)-D-mannan extracted from fruit bodies of *Dictyophoria indusiata* Fisch, also exhibited anti-tumor activity. Hara et al., *Carbohydrate Research*, 143: 111 (1982). It appears that anti-tumor action depends on the type of polymer main chain and its degree of polymerization, because β-(1→3)-glucan-type polymers show higher anti-tumor activity than β-(1→4)-glucan and hemicellulosic polymers. Matsuzaki et al., *Makromol. Chem.*, 187: 325-331 (1986). A carboxymethylated derivative of β-(1→3)-glucan obtained from bacterial culture filtrate caused severe cell loss from established sarcoma 180 tumors within 2 hours after the injection of the derivative. Baba et al., *Journal of Immunopharmacology*, 8: 569-572 (1986). The same author observed a compensatory increase in polymorphonuclear leukocytes due to injection of the substance. Incidentally, bestatin, a dipeptide known to possess immune-modulating and anti-tumor activity (Ishizuka et al., *Journal of Antibiotics*, 32: 642-652 (1980)), influenced neither the tumor yield nor the polymorphonuclear leukocyte count. Baba et al., supra.

There are numerous reports on the anti-tumor effect of sulfated polysaccharides, including heparin (Jolles et al., *Acta Univ. Int. Cancer*, 16: 682-685 (1960); Suemasu et al., *Gann*, 61: 125-130 (1970)). sulfated laminaran and dextran Jolles et al., *British Journal of Cancer*, 17: 109-115 (1963). Yamamoto et al. (*Japanese Journal of Experimental Medicine*, 54: 143-151 (1984)) reported enhancement of anti-tumor activity of a fucoidan fraction by further sulfation. The sulfated product demonstrated activity against L-1210 leukemia. The authors postulated that the mechanism of the anti-tumor action might be due partly to inhibition of invasive growth of L-1210 cells, as a result of electrostatic repulsion between the tumor cell and mesothelial cells. Yamamoto et al., supra. Polysaccharides with sulfate groups are also reported to be human T cell mitogens and murine polyclonal B cell activators Sugawara et al., *Microbiological Immunology*, 28: 831-839 (1984). Generally, homopolysaccharides of high molecular weight with sulfate groups possess these properties. Dorries et al., *European Journal of Immunology*, 4: 230-233 (1974); Sugawara et al., *Cell Immunology*, 74: 162-171 (1982).

It has been reported that glucan extracted from the yeast *Saccharomyces cerbisiae* is a modulator of cellular and humoral immunity. Wooles et al., *Science*, 142: 1078-1080 (1963). The polysaccharide also stimulated proliferation of murine pluripotent hematopoietic stem cells, granulocyte macrophage colony-forming cells, and cells forming myeloid and erythroid colonies. Pospisil et al., *Experientia*, 38: 1232-1234 (1982); Burgaleta et al., *Cancer Research*, 37: 1739-1742 (1977). Maisin et al. (*Radiation Research*, 105: 276-281 (1986)) also reported that IV administration of a polysaccharide induced protection of murine hematopoietic stem cells against x-ray exposure, thereby decreasing the mortality of the mice so exposed.

Seljelid et al., (*Experimental Cell Research*, 131: 121 (1981)) have observed that insoluble or gel-forming glycans activated macrophages in vitro, whereas the corresponding soluble glycans did not. They postulated that the orientation in which the glycan was presented to the mononuclear phagocyte was decisive for activation. Bogwald et al. (*Scandinavian Journal of Immunology*, 20: 355-360 (1984)) immobilized glycans that had a stimulatory effect on the macrophages in vitro. This led the authors to believe that the spacial arrangement of the glycan was decisive for the effect on the macrophages in vitro. A purified polysaccharide isolated from *Candida albicans* induced an antibody response by human peripheral blood lympocytes in vitro. Wirz et al., *Clinical Immunology and Immunopathology*, 33: 199-209 (1984). There were significant differences between the anti-candida antibodies in sera of normal and candida-infected individuals. Wirz et al., supra.

The anti-viral activity of polysaccharides and polysaccharides linked to peptides has been observed. Suzuki et al., *Journal of Antibiotics*, 32: 1336-1345 (1979). Suzuki et al., supra, reported an antiviral action of peptidomannan (KS-2) extracted from culture mycelia of *Lentinus edodes*. Both oral (PO) and intraperitoneal (IP) administration increased the peak serum interferon titer, which protected mice against viral infections. This was different from dextran phosphate (DP-40) (Suzuki et al., *Proceedings of the Society For Experimental Biology and Medicine*, 149: 1069-1075 (1975)) and 9-methylstreptimidone (9-MS) (Saito et al., *Antimier, Agent & Chemotherapy*, 10: 14-19 (1976)), which induced higher titers of interferon in mice only if administered intravenously (IV) or intraperitoneally (IP) to mice.

Anti-inflammatory activity of Aloe vera gel has been widely reported by both oral testimonies and respected scientific journals. Rubel (*Cosmetics and Toiletries*, 98: 109-114 (1983)) discussed fully the possible mechanism of the anti-inflammatory effect of aloe gel. Ukai et al., (*Journal of Pharmacobio-Dynamics*, 6: 983-990 (1983)) noted anti-inflammatory activity of polysaccharides extracted from fruit bodies of several fungi. The polysaccharides demonstrated a significant inhibitory effect on carrageenan-induced edema. One of the polymers, O-acetylated-D-mannan (T-2-HN), in addition demonstrated a more marked inhibitory effect than phenylbutazone on scald hyperalgesia. Ukai et al., supra. The assertion that the polysaccharide is free from protein and lipids strongly suggests that the anti-inflammatory effect is due to the acetylated mannan only. Other researchers have also reported anti-inflammatory effects of complex polysaccharides (Saeki et al., *Japanese Journal of Pharmacology*, 24: 109-118 (1974)), glycoproteins (Arita et al., *Journal of Pharmacology*, 24: 861-869 (1974)) and sulfated polysaccharides (Rocha et al., *Biochemical Pharmacology*, 18: 1285-1295 (1969)).

Literature reports that polysaccharides possess pharmacological and physiological activities continue to flood the pages of well respected scientific journals. It is therefore, not illogical that the mucilaginous gel of the Aloe vera, which is essentially a polysaccharide, holds the secret to Aloe vera's medicinal properties. The discrepancies over whether the polysaccharide is a glucomannan, mannan, pectin or of some other composition are a result of chemical purification steps. By processing aloe according to the present invention, a partially acetylated polymannose has been consistently isolated as the major polysaccharide with pharmacological activity. Yagi et al., (*Planta Medica*, 31: 17-20 (1977)), using a slightly modified extraction method, isolated acetylated mannan (aloe mannan) from *Aloe arborescens* Miller var. *natalensis*. Ovodova (*Khim. Prior. Soedin*, 83: 93833 (1975)), however, earlier isolated pectin as the main component of the same aloe species.

SUMMARY OF THE INVENTION

The present invention is directed to a process whereby the active chemical substance in the aloe plant is physically extracted from whole aloe leaves. The chemical substance is substantially non-degradable and can be administered in a prescribed amount.

The present invention is also directed to the active chemical substance in the aloe plant in the form produced by the process described above. The active chemical substance has been found to be a substantially non-degradable lyophilized ordered linear polymer of acetylated mannose monomers. The mannose monomers are preferably bonded together by $\beta$-(1→4) bonds. The active chemical substance has been measured, standardized and characterized by analytical chemistry techniques.

The term "active chemical substance" as used herein means the substance which is responsible for the wound healing and other beneficial properties of aloe vera. The term which decreases in molecular weight by less than 5 percent over a period of two year and a product which maintains more than 95 percent of its biological activity over a period of two years. The term "substantially acetylated mannose monomers" as used herein means partially or substantially completely acetylated mannose monomers.

The process of the present invention is one for extracting the active chemical substance in the aloe plant from a leaf of the aloe plant which process basically comprises at least the following steps:

(a) washing an aloe leaf in a bacteriacidal solution to remove substantially all surface dirt and bacteria;
(b) removing at least a first end portion from said washed leaf;
(c) draining, preserving and collecting anthraquinone rich sap from said cut and washed leaf;
(d) removing rind from said leaf to produce a substantially anthraquinone-free aloe gel fillet;
(e) grinding and homogenizing said substantially anthraquinone-free aloe gel fillet to produce substantially anthraquinone-free aloe juice having solubilized matter;
(f) adding a water soluble, lower aliphatic polar solvent to the aloe juice to precipitate the active chemical substance and thereby to form a heterogeneous solution;
(g) removing the water soluble, lower aliphatic polar solvent and the solubilized matter from the heterogeneous solution to isolate the precipitated active chemical substance; and
(h) drying the precipitated active chemical substance.

One skilled in the art will appreciate that one may obtain aloe juice having solubilized matter from aloe leaves in whatever manner possible, and then subject this juice to steps (f), (g), and (h) to extract the active chemical substance.

Indeed, one skilled in the art will appreciate that instead of steps (b), (c) and (d), one may instead (b) crush the washed aloe leaves and (c) dialyze the crushed leaves chemically removing unwanted fractions, i.e., anthraquinones, minerals and acids, and the rind to produce a substantially anthraquinone-free gel that may then be subjected to steps (e), (f), (g) and (h) to extract the active chemical substance.

One skilled in the art will also appreciate that instead of steps (b), (c), (d) and (e), one may instead crush the washed aloe leaves and extrude anthraquinone-rich aloe juice having solubilized matter and then subject the aloe juice to steps (f), (g) and (h) to extract the active chemical substance. The active chemical substance is effectively separated from anthraquinones and deleterious ions by this process since the anthraquinones and ions are water soluble and remain in the liquid solvent phase and do not precipitate.

One skilled in the art will also appreciate that instead of steps (b), (c), (d) and (e), one may instead grind the whole washed aloe leaves, filter out fibrous material, and homogenize the remainder to produce anthraquinone-rich aloe juice having solubilized matter. The aloe juice can then be subjected to steps (f), (g) and (h) to extract the active chemical substance. The active chemical substance is effectively separated from anthraquinones and deleterious ions by this process for the reasons noted above.

One skilled in the art will appreciate that an additional process for extracting the active chemical substance in the aloe plant from a leaf of the aloe plant comprises the following steps:

(a) washing an aloe leaf in a bactericidal solution to remove substantially all surface dirt and bacteria;
(b) removing rind from said leaf to produce an aloe gel fillet;
(c) grinding and homogenizing said aloe gel fillet to produce aloe juice having solubilized matter;
(d) adding a water soluble, lower aliphatic polar solvent to the aloe juice to precipitate the active chemical substance and thereby to form a heterogeneous solution;
(e) removing the water soluble, lower aliphatic solvent and the solubilized matter from the heterogeneous solution to isolate the precipitated active chemical substance; and
(f) drying the precipitated active chemical substance.

As noted above, the active chemical substance is effectively separated from anthraquinones and deleterious ions by this process since all the anthraquinones and all the ions are water soluble and remain in the liquid solvent phase and do not precipitate.

Removal of "substantially all surface dirt and bacteria" means (1) removal of dirt to the extent that remaining dirt is less than 0.1% by weight of the weight of the leaf and (2) killing such surface bacteria that the remaining surface bacteria are less than 100 count per gram of leaves.

Furthermore, my preferred process may further comprise the step of ultrafiltration in order to osmotically adjust the aloe juice or aloe vera fraction, or to reduce even further the levels of anthraquinones to less than 5 ppm, even down to less than 100 parts per billion by weight.

These steps enable the processor to use large or small leaves (even less than one year old) because the polymer size found in the mature leaves can be selected and processed out of smaller, immature leaves.

One of the advantages of the instant process is that damaged leaves previously considered unusable due to strong winds or poor collection techniques can be processed, and the undesirable contaminants can be dialyzed out.

The ultrafiltration (dialysis) step incorporates membrane technology that allows the selection of filters with different pore sizes, depending on the condition of the cut aloe leaves, that can accomplish any combination of the following:

(1) A small pore size filter (preferably 100 Daltons) that separates out water and salts from the aloe vera gel, if needed.

(2) Larger pore size filters (preferably 500 Daltons) that can separate out the acids from the aloe vera gel, if needed.

(3) Even larger pore size filters (preferably 2000 Daltons) that can separate the yellow sap components from the aloe vera gel, if needed.

(4) And even larger pore size filters (preferably from 10,000–100,000 Daltons that can size the gel matrix polymers, and divide them out by molecular weight.

A Romicon® 4-column (Romicon Co., 100 Cummings Park, Woburn, Mass. 01801, Model No. HF4 SSS, Membrane Type PM50, Membrane Nos. H526.5 - 43 - pm50) as an ultrafiltration device is recommended.

As an additional preferred embodiment, the washing step of the process may comprise washing the substantially anthraquinone-free aloe gel fillet in a tumbler washer prior to grinding said fillet.

During all of the above-described processes of extracting the active substance from aloe vera gel, minor amounts of organic and inorganic substances are found to co-precipitate with the product. A large fraction of the inorganic salts comprise calcium oxalate. The presence of inorganic salts such as calcium oxalate should be eliminated or at least minimized, for consistency of product and health reasons. It has now been surprisingly found that by adding an effective amount of a mineral acid to adjust the pH of the gel to about 3.0 to about 3.5 prior to addition of alcohol results in a product having a substantially lower level of oxalates and other inorganic salts. Accordingly, it is preferred in all of the above processes for extracting the active chemical substance in the aloe plant from a leaf of the aloe plant, that the pH of the gel be adjusted from about 3.0 to about 3.5 prior to the addition of alcohol.

Preferably, in all the above processes for extracting the active chemical substance in the aloe plant from a leaf of the aloe plant, four volumes of the water soluble, lower aliphatic polar solvent are added to one volume of aloe juice to precipitate the active chemical substance. Preferred water soluble, lower aliphatic polar solvents are methanol, ethanol and propanol. The most preferred solvent is ethanol. One skilled in the art will recognize that other water soluble, lower aliphatic polar solvents may be substituted for the preferred solvents, as long as the active chemical substance will precipitate therefrom.

It is preferred in the above extraction processes that the active chemical substance is allowed to precipitate from the water soluble, lower aliphatic polar solvent and aloe juice mixture for about four hours. It has been determined that allowing the mixture to precipitate for four hours gives the optimum yield of active chemical substance and that after four hours the precipitated active chemical substance begins to degrade. It has also been determined, however, that significant amounts of active chemical substance have been recovered after a precipitation period of 24 hours. One skilled in the art will appreciate that the optimum precipitation time period is dependent on ambient temperature and pressure as well as the nature of the water soluble, lower aliphatic polar solvent.

It is also preferred in the above extraction processes that the precipitated active chemical substance be dried by lyophilization rather than by oven drying since heat may aid in the hydrolysis or degradation of the active chemical substance.

In all of the above extraction processes, any fibrous material (cellulose) contained in the aloe juice is also precipitated by the water soluble, lower aliphatic polar solvent but is precipitated early with the addition of the solvent and is less dense than the active chemical substance. The fibrous material remains on the surface of the solvent after the active chemical substance has been allowed to settle and can therefore be removed quite easily. One skilled in the art will appreciate that one may instead filter the aloe juice to remove fibrous material prior to the addition of solvent.

More preferably, in all of the above processes, aloe leaves or whole plants may be collected from the field sufficiently clean to eliminate a washing step.

The dried, precipitated active ingredient, optionally, may be irradiated by gamma or microwave radiation whereby said active chemical substance is sterilized and preserved.

Accordingly, the present invention is believed to provide new and improved methods for the production of aloe vera products.

The present invention furthermore is further believed to provide new and improved methods for processing the leaf of the aloe vera plant in a manner which avoids the undesirable combination or mixture of distinctively characteristic portions of such plant leaf.

The present invention moreover is believed to provide new and improved processes for preparing various extracts of the leaf of the aloe vera plant which minimizes the concentration of undesirable components in the finished extracts.

The present invention also is believed to provide new and improved processes for preparing extracts of the leaf of the aloe vera plant which maximize the concentration of certain components characteristic of particular portions or segments of the leaf while minimizing or eliminating certain components characteristic of other portions or segments of the leaf.

The present invention also provides new and improved processes for preparing extracts from the leaf of the aloe vera plant which are low in concentration of yellow sap of the leaf.

The present invention finally is thought to provide a method for extracting the active chemical substance in aloe vera gel. This chemical substance has utility as a non-toxic immune stimulating compound. The substance shall hereinafter be referred to as CARRISYN® extract or acemannan. As mentioned above, acemannan has been found to be a substantially nondegradable lyophilized linear polymer of acetylated mannose monomers which standardized and characterized by analytical chemistry techniques.

DESCRIPTION OF THE FIGURES

FIG. 3 shows a schematic of a preferred leaf washing apparatus used in the process of the present invention.

FIG. 4 shows a schematic of a preferred apparatus for sectioning and soaking of aloe vera leaves.

FIG. 19 shows a GLC chromatogram of a standard mixture of rhamnose, fucose, arabinose, xylose, mannose, galactose, glucose and inositol as their glycitol acetates.

DETAILED DESCRIPTION OF THE PREFERRED EMBODIMENTS

Figure 1:
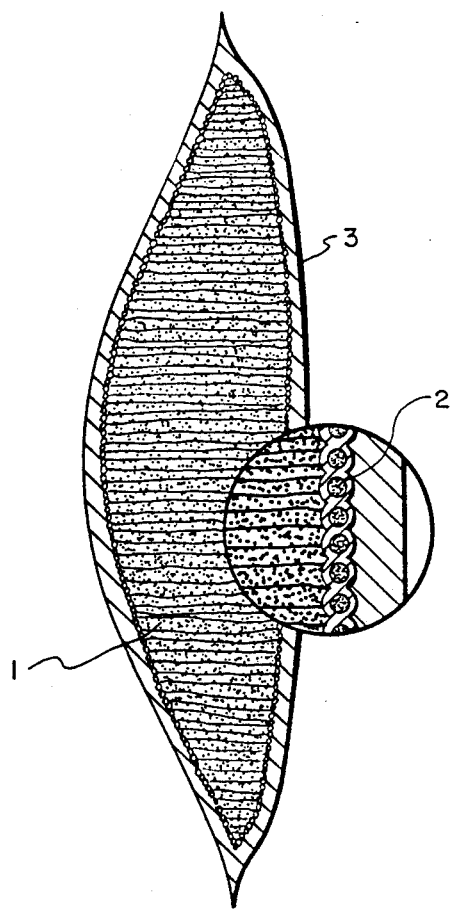
FIGS. 1 and 2 show cut-away portions of an aloe vera leaf.
Figure 2:
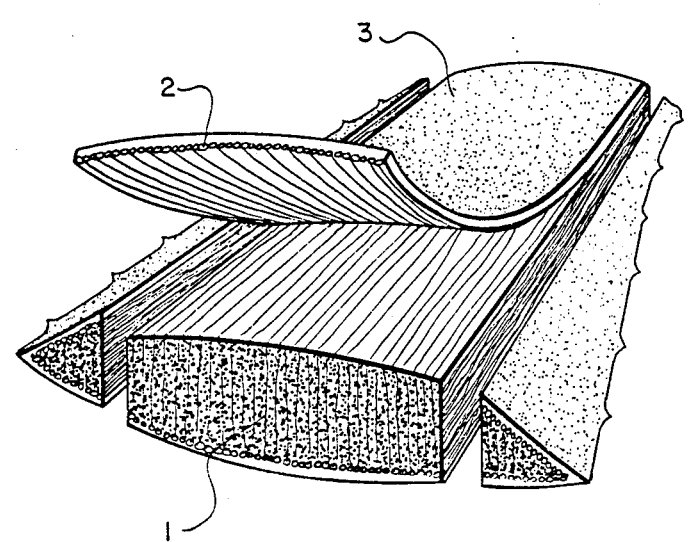

It has been discovered and recognized that sub-portions of the yellow sap and internal gel matrix have characteristics which are unique to those sub-portions, the extracts therefrom therefore having potentially distinct uses from one another. A summary of these distinct portions, and some of their characteristics and potential uses is as follows:

| PORTION | SUB-PORTION | UTILITIES |
| --- | --- | --- |
| Yellow Sap | (1) Sediment | laxative, antifungal, antibiological, pesticidal and sunscreen |
| | (2) Supernatant | mucosal protective action, sunscreen |
| Internal Gel Matrix | (1) Mucilage | penetrant, hypoallergenic, moisturizer |
| | (2) Gel Fillets | ulceroprotective, cell stimulative moisturizer, wound healing |
| | (3) Interstitial Fibers | natural preservative, hemostat |
| | | -continued |

| PORTION | SUB-PORTION | UTILITIES |
| --- | --- | --- |
| Outer Rind | (4) Residual Matrix | cell growth stimulant pesticidal insect repellent, paper pulp fiber |

Based upon the aforementioned knowledge and recognition, and in order to optimize the quality and concentration of the desired components in the final extract depending upon the intended use thereof, the process of this invention is directed to the initial fractionating of the leaves of the aloe vera plant into the particular distinct portions and sub-portions defined above, as well as the separation and isolation of particular components of such sub-portions defined above. The specific details and features of such processes will become more readily understood and appreciated from the following detailed description. The present invention is also directed to particular components that are isolated by the above-mentioned processes.

The products produced by the process of the present invention are preferably obtained from the outer, lower leaves of mature, outdoor grown aloe vera plants. A two year old plant is normally mature; however, the broader leaves of a four or five year old plant typically contain larger amounts of the desired extracts and are also easier to handle. Four or five year old leaves of *Aloe barbadensis* Miller grown in the Rio Grande Valley of Texas are most preferable. These leaves generally weigh about 1½–2½ pounds each. Depending upon the particular use or products that are desired, the leaves can be processed immediately after cutting them from the plant or they can be stored under appropriate conditions for varying time periods before they are processed. Additionally, concentration of various components of the leaf is affected by seasonal variations and the environmental conditions to which the leaves are subjected, all of which should be taken into consideration depending upon the specific intended use to which the plant extracts are to be directed.

The leaves should be pulled or cut from near the base of the plant, preferably without breaking or damaging any part of the leaf prior to processing. One preferably employs a small knife of less than 6 inches, e.g., a pocket knife and cuts the leaf at the base immediately above the stalk, and peels the leaf from the stalk in order to prevent leakage of the clear cellular gel or contamination of the gel with the yellow sap. Any breakage or bruising of the leaf can result in the undesirable comingling of the distinct portions, and therefore, component characteristics of the leaf.

After removal from the plant, the leaves are normally cleaned by washing them with a mild scrubbing action or spraying with a suitable detergent solution (e.g., we prefer OLYMPIC POOL CHLOR 65 ®, distributed by York Chem Co., Dallas, Tex.). In some instances, the cleaning takes place with the aid of soft brushes. After cleaning, the leaves are rinsed thoroughly in clean water to remove any vestige of any detergent solution.

The bottom white or light colored portion of each leaf and the upper tip portion thereof are removed by cutting carefully with a small sharp knife. These portions, essentially constituting the ends of the leaf, may be separately processed to obtain the yellow sap therefrom for those applications in which it is desired to produce products having components with the yellow sap characteristics referred to above.

The remaining portion of each aloe vera leaf is then crosscut into short segments, preferably one-half inch in length, and each segment is placed upright in an aqueous solution (preferably deionized water) which may be hypertonic, isotonic or hypotonic, resulting in the yellow sap draining from the segments. Alternatively, in those applications in which it is desired to collect the yellow sap for use in other preparations having the characteristics noted above, the segments may be placed upright in a dry collection container, preferably of stainless steel with a stainless steel wire mesh bottom to allow drainage and for water contact to allow the water to dialyze the leaves.

The segments are permitted to drain for approximately twenty to thirty minutes in this manner. The cut segments will eventually form a seal and cease draining. The yellow sap that is collected will then, upon standing for an appropriate period of time, separate into two sub-portions, namely sediment and supernatant, respectively. The yellow sap is useful for making a good sunscreen on intact skin (not broken skin) and provides the skin with an olive tan color, and is also useful for the manufacture of laxatives.

After completion of the procedures which remove the yellow sap from the cut leaf segments, the segments are then pared to form fillets utilizing any suitable equipment such as a wire (i.e., consumer cheese) slicer or paring blades (e.g., paring knife) to remove the outer rind or skin of the leaf segments and the layer that is immediately below such outer skin. The leaf segments may be frozen to facilitate this skinning procedure. After paring, what remains is the internal gel matrix portion (fillet), and this portion is inspected and hand cleaned to remove any adhering skin or discolored portions to eliminate any residual yellow sap therefrom. One uses a mild water spray, preferably deionized water (and free of alcohol) or submerges the gel matrix portion under flowing clean water, to facilitate removal of such yellow sap residuum.

The resultant fillet (internal gel matrix) can then be drained for approximately an hour. During this draining procedure, a slimy coating usually forms on the surfaces of the gel matrix, this coating being collected by gravity or assisted by appropriate means such as centrifugation. This collected coating is the mucilage sub-portion referred to above.

The remainder of the gel matrix, in the form of gel matrix strips, may then be ground, shredded or blended to break up the interstitial fibers present therein, or the gel matrix strips may be forced through a wire mesh or filter screen in order to achieve liquefaction. This resultant substance may then be subsequently homogenized. Alternatively, the gel matrix strips may be frozen and thawed and subsequently mixed to produce a liquid substance with fibers (such substance constituting the gel fillets sub-portion referred to above). This substance can then be filtered to obtain the interstitial fibers sub-portion, leaving the residual matrix sub-portion referred to above.

The homogenized extract thus obtained typically has a pH of approximately about 4 to about 5, preferably about 4.

All steps in the process described are performed at about room temperature.

FIGS. 3-7 disclose, in even further detail, preferred embodiments of the instant process. Specifically, in FIG. 3, there is disclosed apparatus for leaf washing. Aloe vera leaf washing equipment (Thompson Manufacturing Company, Harlington, Tex.) A is utilized whereby leaves are first presoaked in vat 4. The whole leaves α are then placed by hand onto a conveyor belt 8 by which they are pulled underneath two brushes 9a and 9b. Conveyor belt 8 is driven via a chain 7 which is rotated on a second end by motor and pulley 6 which extends from a housing 5, also provided by Thompson Manufacturing Company. As the leaves are brushed and washed, upon passing through the second brush 9b, the leaves are inspected at the end 10 of conveyor belt 8, by which the leaves are visually inspected and determined whether or not they are sufficiently clean. If the leaves are not sufficiently clean, they are placed into vat 12 for further washing; if the leaves are sufficiently clean, they are placed upon an upwardly moving conveyor B having steps 13 for which each individual leaf may be further washed with tap water by sprayers 11. The conveyor B is provided by Dallas Mill Wright Co. of Seagoville, Tex. The rinse sprayers 11 are provided by Key Plumbing, Seagoville, Tex. Stainless steel vat 12 is made of 316 stainless steel and is custom made by the National Sheet Metal Company of Dallas, Tex.

After washing, as indicated in FIG. 4, the leaves are sectioned and soaked. After moving up through steps 13 of conveyor B, the clean, raw leaves α drop onto a tray 14 which is provided with a hole 15 for removal of trash. Tray 14 is part of a sectioning and soaking apparatus C of 316 stainless steel provided by the National Sheet Metal Company of Dallas, Tex. This equipment is custom fabricated. On tray 14 the leaves are manually sectioned at both ends with the tips and butts disposed through the hole 15 into a trash receptacle (not shown). The cut leaves β are then stacked into any one of a number of baskets 16 of stainless steel each having a wire mesh bottom made of stainless steel. Then these baskets 16 are placed in a stainless steel track which forms the top part of a trapezoidal funnel 17 by which yellow sap is drained from the bottom of the leaves through the baskets, falling into the bottom portion of the funnel 17. The yellow sap is periodically removed and is kept frozen for storage. The yellow sap draining step takes about 30 minutes.

After this step, the cut leaves β, still retained in basket 16, are manually moved to water bath 18 at positions closest to trapezoidal funnel 17. In countercurrent flow, water comes into bath 18 through inlet water pipe 19, at a point farthest removed from trapezoidal funnel 17 and is subsequently removed through exit water pipe 20 at a position closest to trapezoidal funnel 17. Trays are gradually moved manually through the water bath in a direction away from trapezoidal funnel 17, and the washing step whereby the baskets remain in water bath 18 takes approximately one hour.

After washing, the baskets are placed on tray 21 for drying, which lasts for only a few minutes. Again, the entire assembly in FIG. 4, pertaining to the baskets, including wire mesh, yellow sap draining and auto washing equipment, is made of 316 stainless steel, custom fabricated by the National Sheet Metal Company, Dallas, Tex.

Figure 5:
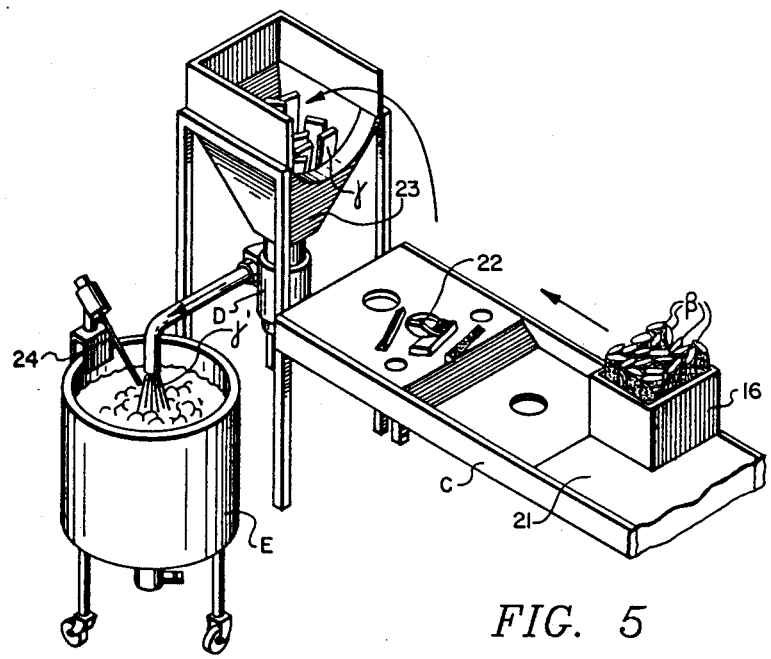
FIG. 5 shows a schematic of preferred apparatus for the cutting of aloe sections into fillets and for coarse grinding.

After washing, the cut leaves β stacked in basket 16 on tray 21 are then moved to an area for further sectioning into fillets, as shown in FIG. 5. Rind 22 is removed from the fillets so that only substantially clear material remains. The rest of the rind 22 is discarded. Fillets γ are then placed into trough 23 which feeds to a rough coarse grinder D. The trough 23 is manufactured of 316 stainless steel by the National Sheet Metal Company of Dallas, Tex. The grinder is a Model No. 5150-N-Sinkerator TM (Watson Food Service Industries, Inc., Dallas, Tex.). After rough coarse grinding through grinder D, the processed material γ emerging from the grinder passes through to a portable tank E of approximately 100 gallon capacity which comprises a vertical single shell tank of 316 stainless steel (Perma-San, Manufacture, distributed through Van Tone, Inc., Dallas, Tex.). Coarse ground fillet γ is agitated in tank E by a Perma-San agitator (Model No. AAPH2), also distributed through Van Tone, Inc. of Dallas, Tex.

Figure 6:
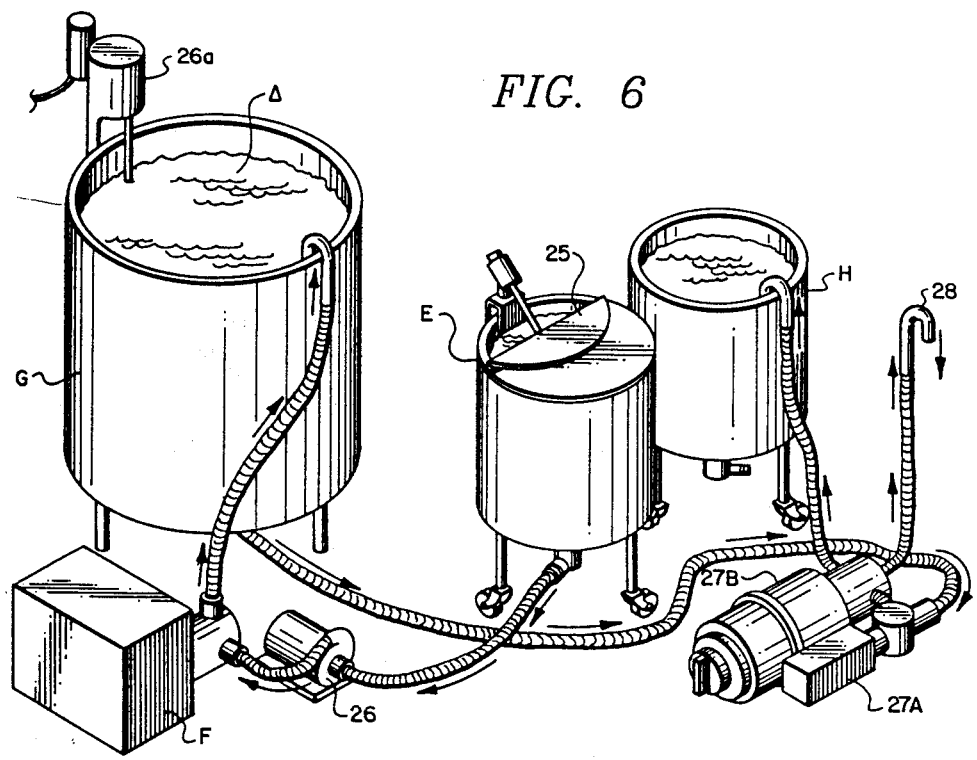
FIG. 6 shows a schematic of preferred apparatus for fine homogenization and filtering.

After rough homogenization, material from tank E is taken to a separate staged area for fine homogenization and (optional) filtering. In FIG. 6, material from tank E is pumped through pump 26 (centrifuge pump provided by Crepaco, Inc., Dallas, Tex., Model No. 4V-81, of stainless steel) driven by Reliance Motor Model No. B76Q2139M-VF of the Reliance Electric Company, Cleveland, Ohio, into a fine homogenizer F (Crepaco, Inc., Dallas, Tex., Model No. 3DD13). After fine homogenization, the material is transported to a large 1,000 gallon vertical single shell mixing tank G made of 316 stainless steel (Perma-San, Manufacturer, distributed to Van Tone, Inc. of Dallas, Tex.). The finely ground fillet Δ is agitated by a Perma-San TM agitator 26a (Perma-San, Model No. AAPH2, distributed through Van Tone, Inc., Dallas, Tex.). Material Δ in tank G may be sent directly to processing for a drinking product for direct human consumption after flavoring and appropriate preservatives are added. In the alternative, material in tank G may be removed and sent to pump 27a which forms one unit with filter 27b for removal of pulp through discard line 28. Pump 27a and filter 27b form the part of a Lomart diatomite filter (Model No. 99-2138 distributed by Allen Recreation Company, Dallas, Tex.). Filtered material is then pumped into tank H, which like tank E, can be provided with a lid 25.

Figure 7:
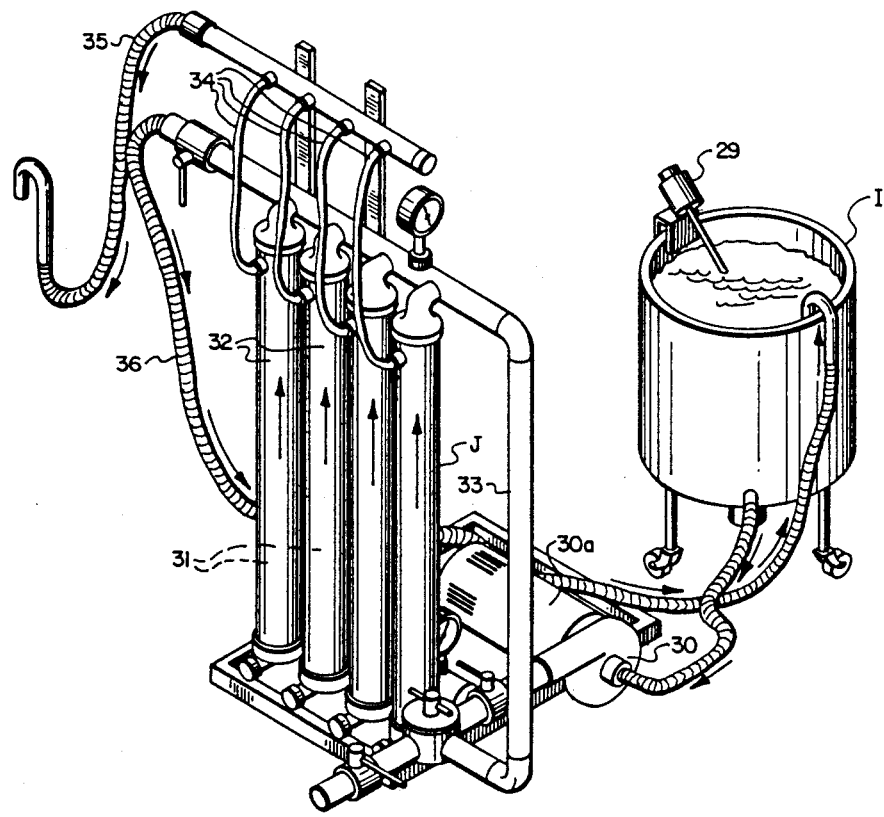
FIG. 7 shows a schematic of a preferred use of dialysis equipment for fine separations of processed aloe material.

In FIG. 7, finely ground fillet Δ is partially filtered, is stirred by mixer 29 and pumped through pump 30 into a dialyzer. Mixer 29 is a Perma-San TM agitator (Model No. AAPH2) distributed through Van Tone, Inc., Dallas, Tex. Pump 30 is a Superior TM stainless steel Model SCS45 process pump (Superior Stainless Company, Delavan, Wis.) Attached to process pump 30 is motor 30a of 3 horsepower made by Baldor Motor of 4450 rpm (Cat. No. CM3559T of the Baldor Electric Company, Ft. Smith, Ark.) Material pumped through pump 30 passes through dialysis unit J, (a Romicon Model HF4SSS ultrafiltation system made by Romicon Inc., Woburn, Mass.) having 4 filters 31 (not shown), each filter housed in filter housing 32. Material passes vertically to a point where portions can be removed through separation lines 34 and into separation discharge lines 35. Other material not separated is recycled through recycle return line 33 back into the dialysis unit, or in the alternative, through separation return line 36 back into the vat I.

Depending on the fraction of aloe desired and end product sought, the desired material can either be obtained through separation discharge line 35 after processing or in vat I. For example, if excess water and minerals need to be removed, a small pore size ultrafilter can be used to separate out the water and minerals which are discharged through line 35 and the desired aloe fraction is returned to vat I. This process can be repeated until the desired amount of salt and water is removed from the product contained in vat I simply by circulating it through the dialysis unit. This process can include more than one dialysis step. For example, as previously described, the salts, low molecular weight acids and unwanted anthraquinones can be removed in a first dialysis step. The unwanted material is discharged through separation discharge line 35 and the desired fraction is returned to vat I. This step is accomplished by using ultrafilters obtained from Romicon with 10,000 Dalton pores. Next, the 10,000 Dalton ultrafilters are replaced with 50,000 Dalton ultrafilters also obtained from Romicon and the dialysis process is repeated. The dialysis process now separates the gel matrix polymers into two fractions; a first fraction consists of gel matrix polymers ranging in size from 10,000 to 50,000 Daltons and is discharged through separation discharge line 35, a second fraction consists of gel matrix polymers greater than 50,000 Daltons in size and is returned to vat I. This process can last from minutes to hours depending upon the amount of salt and water that is needed to be removed from a given product.

In FIG. 7, separation return line 36 is made of Tygon tubing (food grade) provided by the Texas Rubber Supply Company, Dallas, Tex. The separation discharge line 35 is a 316 stainless steel pipe distributed by Van Tone, Inc., Dallas, Tex.

The residual matrix sub-portion may then be treated to separate, isolate and purify the active chemical substance, acemannan, in aloe vera gel. To separate acemannan from the residual matrix sub-portion, an excess of a water soluble, lower aliphatic polar solvent is added to the residual matrix sub-portion. Acemannan then begins to precipitate from this mixture. The solution is allowed to settle for a sufficient period of time to allow as much active ingredient to precipitate out of solution as possible but not so long that the supernatant is decanted or siphoned off without disturbing the settled precipitate. The precipitate and remaining solution are then placed in an appropriate centrifuge apparatus and the precipitate is collected into a pellet. After centrifugation, the supernatant is decanted and discarded. Optionally, the pellet is washed with a fresh aliquot of the water soluble, lower-aliphatic polar solvent and collected again and the supernatant is again discarded. The pellet is then lyophilized to dryness and allowed to dry overnight. The resulting product is a substantially non-degradable lyophilized form of acemannan. The resulting product may be ground to form a powder. Preferably, a suitable acid is added to aloe vera gel prior to the addition of the lower aliphatic polar solvent. The acid is added to solubilize calcium oxalate contained in the aloe vera gel in order to facilitate its removal. The acid is preferably added at a strength sufficient to solubilize the calcium oxalate impurity while not degrading the acemannan polymer chain.

An alternate and preferred process for separating and isolating acemannan includes the following steps:

Leaves from mature, outdoor grown aloe vera plants are pulled or cut from near the base of the plant, preferably without breaking or damaging any part of the leaf prior to processing. The leaf is preferably cut at the base of the plant immediately above the stalk and is peeled from the stalk in order to prevent leakage of the clear cellular gel or contamination of the gel with the yellow sap.

After removal from the plant, the butt and tip portions of the leaves are removed and the cut leaves are pared to form fillets as described above in the fractionation process.

The resultant fillet (internal gel matrix) is then ground, shredded or blended to break up the interstitial fibers present therein or the internal gel matrix may be forced through a wire mesh or filter screen in order to achieve liquefaction. The resultant liquefied internal gel matrix is then homogenized. The homogenized extract is then ground, shredded or blended to break up the interstitial fibers present therein or the internal gel matrix may be forced through a wire mesh or filter screen in order to achieve liquefaction. The resultant liquefied internal gel matrix is then homogenized. The homogenized extract thus obtained typically has a pH of approximately 4 to about 5, preferably about 4. The homogenized extract is then filtered to remove the interstitial fibers. The homogenized and filtered extract may then be treated in the identical manner as the residual matrix sub-portion, referred to immediately above, to separate and isolate acemannan An additional and preferred process for separating and isolating acemannan includes the following steps:

Leaves from mature, outdoor grown aloe vera plants are pulled or cut from near the base of the plant, preferably without breaking or damaging any part of the leaf prior to processing. The leaf is preferably cut at the base of the plant immediately above the stalk and is peeled from the stalk in order to prevent leakage of the clear cellular gel or contamination of the gel with the yellow sap.

The leaves may then be crushed by suitable means, for example, a "Thompson Aloe Extruder" made by Thompson Manufacturing Company, Harlingen, Tex., to extrude aloe juice. The extruded aloe juice may then be treated in the identical manner as the residual matrix sub-portion, referred to above, to separate and isolate acemannan.

All steps in the processes described are performed at about room temperature except for the lyophilization step, which is preferably performed at about $-50°$ C.

Various modifications of the disclosed processes and compositions of the invention, as well as alternative modifications, variations and equivalents will become apparent to persons skilled in the art upon reading the above general description. The following examples are illustrative only and are not intended to limit the scope of the appended claims, which cover any such modifications, equivalents or variations.

EXAMPLE 1

Process for Separating and Isolating Acemannan

A. PRELIMINARY WORK:
1. Previously cleaned tanks, mixers and fittings were sanitized with 50% isopropyl alcohol (IPA) solution and rinsed free of IPA with hot deionized water.
2. Pumps and attached hoses were drained with 5% "HTH" chlorine swimming pool solutions, then flushed with water.
3. The pumps and attached hoses were sanitized with 50% isopropyl alcohol solution. Pumps and attached hoses were flushed with hot deionized water until free of isopropyl alcohol.
4. A homogenizer and attached hoses and pumps were sanitized with 50% isopropyl alcohol solution. The homogenizer and attached hoses were flushed with hot deionized water until free of isopropyl alcohol.

*Aloe barbadensis* Miller leaves collected from the Rio Grande Valley were transferred in a refrigerated truck at 40° to 45° F. within eight hours after harvest and stored under refrigeration at 40° to 45° F. until processed to reduce degradation.

Twenty to sixty pounds of stored leaves were then placed in a prewash bath of an aqueous solution of calcium hypochlorite at room temperature, substantially to remove surface dirt from the leaves and kill surface bacteria on the leaves. The aqueous solution of calcium hypochlorite was prepared by adding approximately 0.125 grams of 98% calcium hypochlorite to one liter of water to produce a solution containing 50 ppm of free chlorine. The leaves remained in the prewash bath for a period of approximately five minutes.

Next, the substantially dirt and bacteria free leaves were placed on the horizontal conveyor belt of a "Thompson Aloe Washer" made by Thompson Manufacturing Company, Harlingen, Tex. The "Thompson Aloe Washer" washed the leaves with room temperature water to remove the surface dirt and aqueous solution or calcium hypochlorite from the leaves Again, the leaves were visually inspected and hand scrubbed as necessary to remove any surface dirt remaining on the leaves Such leaves were then rinsed with room temperature water.

The tip and butt portion was then removed from each leaf and the leaves were placed in stainless steel basket-type containers, placed together on top of a funnel shaped stainless steel collector, each container having a mesh bottom. Yellow sap was allowed to drain from the leaves for approximately 30 minutes. The yellow sap passed through the mesh bottom of the stainless steel basket and was collected in a funnel shaped collector.

The stainless steel basket type containers containing the aloe leaves were removed from the collector, and were then submerged in a second stainless steel vessel comprising a room temperature water bath of continuously horizontally flowing rinse water moving countercurrent to the containers which are slowly moved by hand from one end of the vessel to the other, for approximately thirty minutes to one hour. This allows the yellow sap to drain further from the leaves. The leaves must be allowed to soak in this solution for 30 minutes.

The leaves were then removed from this solution and the rind was removed from each leaf with a sharp knife or wire cheese slicer to produce an aloe gel fillet from each leaf portion. The aloe gel fillets were visually inspected and any contaminated aloe gel fillets or fillet parts detected by a characteristic yellowish discoloration were discarded. The total mass of uncontaminated aloe gel fillets was 20 to 60 percent of the starting leaf mass, depending on the leaf size and condition.

The uncontaminated aloe gel fillets were then placed in a 750 seat restaurant set stainless steel garbage disposal unit which coarse ground the fillets to an average particle size of the consistency of a thick, but freely flowing (coarse homogenized) liquid. The stainless steel garbage unit was made by the N-sink-erator TM Division of Emerson Electric Co., Racine, Wis., Model No. SS-150-13, Serial No. 115132.

The coarse ground aloe gel fillets then passed to a stainless steel holding vat. The holding vat was made by Process Equipment Corp. of Belding, Mich., Model No. 100 gallon OVC, Serial No. 40865-3.

From the holding vat, the coarse ground aloe gel fillet solution was pumped to a homogenizer. The homogenizer was made by Crepaco Food Equipment and Refrigeration, Inc., of Chicago, Ill., Serial No. 04-03. The homogenizer was of a type typically used in dairy processes for the homogenization of milk. The coarse ground aloe gel fillet solution was finely homogenized under a pressure of about 1,500 psi.

From the homogenizer, the finely homogenized aloe gel fillet solution was pumped to a stainless steel storage tank. The storage tank was made by Process Equipment Corp. of Belding, Mich., Model No. 1000 gallon OVC, Serial No. 40866-2. The total mass of the homogenized aloe gel fillet solution was 20 to 60 percent of the starting leaf mass. Then, if necessary, the homogenized product was dialyzed using ultrafiltration.

The finely homogenized aloe gel fillet solution was then filtered to remove the interstitial fibers using a Leslie's Diatomaceous Earth Filter Model DE-48. The interstitial fibers themselves, instead of diatomaceous earth, were used as the filter media, the fibers being supported by a nylon mesh cloth filter support. The gel was pumped through the filter for several minutes before opening the exit port so that a sufficient amount of fibers could build up to serve as the filter media.

Twenty gallons of the filtered aloe gel fillet solution was then pumped into a 100 gallon tank and 80 gallons of 190 proof undenatured ethanol (Ethyl Alcohol, 190 proof, U.S.P., punctilious, 54 gal. Batch I.D. #CT185JO4 available through U.S. Industrial Chemicals, Co., P.O. Box 218, Tuscola, Ill. 61953) was added to the aloe gel fillet solution. The solution was stirred for 20 to 30 minutes using a Perma-San propeller agitator model #AAPGF-4A, Process Equipment Corp., Belding, Mich.

The alcohol-gel solutions were then immediately transferred to several 11 quart pans of 10¼" diameter and 8" high of 18-8 stainless steel (Bloomfield Industries Inc., Chicago, Ill., available through Watson Food Service Equipment and Supplies, 3712 Hagger Way, Dallas, Tex.).

The alcohol-gel solutions were then allowed to settle for approximately four hours.

The clear liquid supernatant was then decanted or siphoned off, using care not to disturb the precipitate that had settled on the bottom of the pans. The precipitate and remaining solutions were then transferred to four 1 pint stainless steel centrifuge buckets with about 500 g. of precipitate and remaining solution being transferred to each bucket. The buckets were then spun at $2000 \times g$ for about 10 minutes using an IEC Centra-7 Centrifuge (International Equipment Co., 300 2nd Avenue, Needham Heights, Mass. 02194 available through: American Scientific Products, P.O. Box 1048, Grand Prairie, Tex. 75050).

After centrifugation, the supernatants were decanted and discarded. The pellets were then washed with fresh 190 proof, undenatured ethanol and collected again at $2000 \times g$ for about 10 minutes. After spinning again the supernatant was discarded.

The pellet was then transferred to several 600 ml. VIRTIS lyophilization jars and swirled in liquid nitrogen until frozen. The lyophilization jars were then attached to a lyophilization apparatus consisting of a Welch Duo-seal Vacuum Pump (Model No. 1402, available from Sargeant-Welch, P.O. Box 35445, Dallas, Tex. 75235), a Virtis Immersion Coil Cooler (Model No. 6205-4350 Cooler in acetone bath) and a Virtis 18 Port Vacuum Drum Manifold (Model No. 6211-0350). All Virtis equipment is available from American Scientific Products, P.O. Box 1048, Grand Prairie, Tex. 75050. The lyophilization drum was filled with acetone that was maintained at $-50°$ C.

The samples were lyophilized to dryness overnight and were then weighed on a Mettler AE 163 balance. The samples remaining consisted of substantially non-degradable lyophilized CARRISYN® extract. The yield from 20 gallons of aloe vera gel was approximately 145–155 g. of CARRISYN® extract.

EXAMPLE 2

Process for Separating and Isolating Acemannan

*Aloe barbadensis* Miller leaves collected from the Rio Grande Valley were transferred in a refrigerated truck at 40° to 45° F. within eight hours after harvest and stored under refrigeration at 40° to 45° F. until processed to reduce degradation.

The tip and butt portion was removed from each leaf. The rind was then removed from each leaf with a sharp knife or wire cheese slicer to produce an aloe gel fillet from each leaf portion.

The aloe gel fillets were then placed in a 750 seat restaurant set stainless steel garbage disposal unit which coarse ground the fillets to an average particle size of the consistency of a thick, but freely flowing (coarse homogenized) liquid. The stainless steel garbage disposal unit was made by the N-sink-erator Division of Emerson Electric Co., Racine, Wis., Model No. SS-150-13, Serial No. 115132.

The coarse ground aloe gel fillets then passed to a 100 gallon stainless steel holding vat. The holding vat was made by Process Equipment Corp. of Belding, Mich., Model No. 100 gallon OVC, Serial No. 40865-3.

From the holding vat, the coarse ground aloe gel fillet solution was pumped to a homogenizer. The homogenizer was made by Crepaco Food Equipment and Refrigeration, Inc., of Chicago, Ill., Serial No. 04-03. The homogenizer was of a type typically used in dairy processes for the homogenization of milk. The coarse ground aloe gel fillet preservative solution was finely homogenized under a pressure of 1,500 psi.

From the homogenizer the finely homogenized aloe gel fillet solution was pumped to a stainless steel storage tank The storage tank was made by Process Equipment Corp. of Belding Mich., Model No. 1000 gallon OVC, Serial No. 40866-2. The total mass of the homogenized aloe gel fillet solution was 20 to 60 percent of the starting leaf mass. Then, if necessary, the homogenized product was dialyzed using ultrafiltration.

The homogenized gel was then filtered to remove the interstitial fibers using a Leslie's Diatomaceous Earth Filter Model DE-48. The interstitial fibers themselves instead of diatomaceous earth were used as the filter media, the fibers being supported by a nylon mesh cloth filter support. The gel was pumped through the filter for several minutes before opening the exit port so that a sufficient amount of fibers could build up to serve as the filter media.

Twenty gallons of the filtered aloe gel was then pumped into a 100 gallon tank and 80 gallons of 190 proof undenatured ethanol (Ethyl Alcohol, 190 proof, U.S.P., punctilious, 54 gal. Batch I.D. #CT185JO4 available through U.S. Industrial Chemicals Co., P.O. Box 218, Tuscola, Ill. 61953) was added to the aloe gel fillet solution. The solution was stirred for 20 to 30 minutes using a Perma-San propeller agitator model #AAPGF-4A, Process Equipment Corp., Belding, Mich.

The alcohol-gel solutions were then immediately transferred to several 11 quart pans 10¼" diameter and 8" high of 18-8 stainless steel (Bloomfield Industries Inc., Chicago, Ill., available through Watson Food Service Equipment and Supplies, 3712 Hagger Way, Dallas, Tex.).

The alcohol-gel solutions were then allowed to settle for approximately four hours.

The clear liquid supernatant was then decanted or siphoned off using care not to disturb the precipitate that had settled on the bottom of the pans. The precipitate and remaining solutions were then transferred to four 1 pint stainless steel centrifuge buckets with about 500 g. of precipitate and remaining solution being transferred to each bucket. The buckets were then spun at $2000 \times g$ for about 10 minutes using an IEC Centra-7 Centrifuge (International Equipment Co., 300 2nd Avenue, Needham Heights, Mass. 02194 available through: American Scientific Products, P.O. Box 1048, Grand Prairie, Tex. 75050).

After centrifugation, the supernatants were decanted and discarded. The pellets were then washed with fresh 190 proof, undenatured ethanol and collected again at $2000 \times g$ for about 10 minutes. After spinning again the supernatant was discarded.

The pellet was then transferred to several 600 ml. VIRTIS lyophilization jars and swirled in liquid nitrogen until frozen. The lyophilization jars were then attached to a lyophilization apparatus consisting of a Welch Duo-seal Vacuum Pump (Model No. 1402, available from Sargeant-Welch, P.O. Box 35445, Dallas, Tex. 75235), a Virtis Immersion Coil Cooler (Model No. 6205-4350 Cooler in acetone bath) and a Virtis 18 Port Vacuum Drum Manifold (Model No. 6211-0350). All Virtis equipment is available from American Scientific Products, P.O. Box 1048, Grand Prairie, Tex. 75050. The lyophilization drum was filled with acetone that was maintained at $-50°$ C.

The samples were allowed to dry overnight and were then weighed on a Mettler AE 163 balance. The samples remaining consisted of substantially non-degradable lyophilized CARRISYN® extract. The yield from 20 gallons of aloe vera gel was approximately 145-155 g. of CARRISYN® extract.

EXAMPLE 3

Standard Laboratory Scale Process for Separating and Isolating CARRISYN® Extract Approximately 50 pounds of *Aloe barbadensis* Miller leaves were washed with water and brushed to remove dirt, dried latex and other contaminants The outer cuticle of each leaf was then removed and the whole fillets were placed in a large beaker (on ice).

In 1.5 liter batches, a Waring blender was loaded with the whole aloe fillets. The fillets were blended at high speed twice, for two minutes, at room temperature. The blended fillets were then cooled at 4° C. to allow foam, generated during blending, to settle.

The blended aloe juice was then filtered through four layers of cotton (Cleveland Cotton) to remove any fibrous cellulosic pulp. The filtrate was then passed through six layers of cotton and approximately 4 liters of aloe juice was collected.

The aloe juice was then placed in a large five gallon stainless steel container. To the filtered juice was added 16 liters of chilled ethanol (Fisher Ethanol reagent grade, Cat. No. A995). The ethanol was added slowly while stirring the aloe juice. A flocculent precipitate formed and the mixture was stirred for 15 to 30 minutes and was allowed to settle at room temperature for about two hours.

The supernatant was then decanted off, and the pellet was placed in a small blender to which one liter of deionized water was added. This mixture was blended for several minutes at low speed to wash the pellet and was then placed in an eight liter nalgene container. To this mixture was added four more liters of ethanol and the mixture was stirred for 30 minutes. The precipitant that formed was allowed to settle for about two hours.

The majority of the supernatant was then decanted off and the resultant pellet was centrifuged at $2000 \times g$ for 20 minutes at room temperature to pellet the precipitant for easy decanting of the remaining solvent.

The pellet was then placed in a lyophilization flask and lyophilized overnight in a Virtis lyophilizer.

The lyophilized powder weighed 10.9 g. The percent yeild was 0.273% or $2.73 \times 10^{-3}$ g/ml.

EXAMPLE 4

The Reduction of Calcium Oxalate Contaminant In Aloe Vera Extract—Acemannan

During the process of extraction of acemannan from aloe vera gel by alcohol, minor amounts of organic and inorganic substance are found to co-precipitate with the product. A large fraction of the inorganic salts and indeed the major comtaminant in the alcohol extraction of aloe vera gel to acemannan is calcium oxalate. The presence of calcium oxalate is confirmed by optical microscopy, infrared spectroscopy and thermogravimetric analysis. Although the quantity of calcium oxalate may vary from batch to batch, calcium oxalates accounting for about 30% of the total extract by weight have been observed. The purpose of the process described in Example 4 is to reduce the oxalate content in acemannan. Calcium oxalate is very insoluble in water and alcohol. By treating aloe gel with alcohol, the oxalate in the CARRISYN® extract precipitate is concentrated. This concentration of oxalate is demonstrated by the strong infrared absorption of CARRISYN® extract between 1600-1587 $cm^{-1}$ due to the carbonyl assymetric stretch of the oxalate and the high ash content of CARRISYN® extract from thermogravimetric analysis. Since the acemannan is the active substance in CARRISYN® extract, inorganic salts such as calcium oxalate should be eliminated or at least minimized for consistency of product quality and for health reasons.

One procedure for separating the oxalates and other inorganic salts would be by membrane dialysis However, this method has many drawbacks and disadvantages The process is very time consuming since the crude CARRISYN® extract must be rehydrated, re-extracted in alcohol and freeze dried again. Most importantly, unless the product is preserved during the dialysis step, microbial degradation and spoilage will result in very inactive CARRISYN® extract.

Generally, carboxylic acid salts are converted to their corresponding acids when treated with dilute mineral acids. By treating calcium oxalate with hydrochloric acid, oxalic acid and calcium salts of oxalic acid would be produced according to the following mechanism:

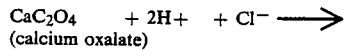

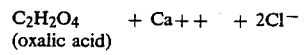

Oxalic acid is highly soluble in water and alcohol and is therefore preferentially extracted into the water/alcohol misture. The result is that the CARRISYN ® extract has a much lower level of oxalates and other inorganic salts.

About 2 liters of Aloe vera gel previously homogenized at 500 psig and filtered through a new swimming pool filter was collected for this Example. An initial pH of the gel was taken after stirring. Gel samples of known weight were placed into several 600 mL beakers and the pH adjusted as appropriate with a suitable acid, here a dilute mineral acid (preferably 6N hydrochloric acid) or concentrated sodium hydroxide solution, as follows:

| Sample # | 0 | 1 | 2 | 3 | 4 | 5 | 6 | 7 | 8 |
|---|---|---|---|---|---|---|---|---|---|
| Weight (gel) | 100. | 100. | 99.3 | 100. | 100. | 99.7 | 100. | 99.9 | 99.5 |
| pH | 4.56 | 4.07 | 2.45 | 3.35 | 5.09 | 10.6 | 6.16 | 7.0 | 8.58 |

After a pH of each sample was adjusted, four (4) volumes of SDA-3A ethanol were added as soon as possible to minimize the time the gel would be under the stipulated pH condition. After stirring the mixture for less than 2 minutes, each mixture was allowed to stand for about 3-4 hours. Each extract was then centrifuged, freeze dried and weighed to determine the yield under the various pH conditions.

The infrared spectra of the nine solid CARRISYN ® extract samples were obtained from a disc made by mixing an appropriate amount of the substance in potassium bromide. Each disc was scanned from 4000 to 400 cm$^{-1}$ (wave numbers) on an IBM FT-IR spectrometer. The spectra of the CARRISYN ® extract samples at different pH conditions were compared qualitatively.

Thermogravimetric Analysis:

The thermal weight loss of CARRISYN ® extract has a definite finger print profile. About 10 milligrams of each sample was heated in a Mettler thermoanalyzer from 25° C. to 780° C. at a rate of 20° C./min. Nitrogen gas atmosphere was used until a temperature of 600° C. was reached, followed by oxidizing environment at 780° C. and then each sample was allowed to remain at this temperature for 2 minutes. From the weight loss thermogram, the moisture content, the carbohydrate, oxidizable carbon skeleton, oxalate and ash contents were determined.

Results and Discussion:

The most important factor with an acid treatment of CARRISYN ® extract is whether the physiochemical properties of the substance have been adversely affected by the process. A suitable acid must be selected: (i) an acid capable of achieving the proper pH range (from about 3.0 to about 3.5) in reasonable volumes, (ii) will not react adversely with beneficial components (polydisperse acemannan), the solvent mixture (ethanol) and the holding vessels and equipment; and (iii) additionally, chosen in such a concentration as not to degrade the acemannan chain. Many dilute mineral acids and organic acids in higher concentrations are suitable, although a non-oxygenated mineral acid is most suitable as esterification and degradation are minimized. With the selection of a suitable acid, e.g., 6N hydrochloric acid, rather than having an adverse effect, the quality of CARRISYN ® extract appears to improve appreciably at lower pH conditions For example, the same concentration (w/v) of CARRISYN ® extract gave a more viscous, rehydrated solution when acid treated A viscous solution signifies good product. Size exclusion chromatographic separation of the solution demonstrated the same chromatographic profile as an untreated CARRISYN ® extract. Therefore, under the conditions applied, degradation was not observed The following results demonstrate that the yield of CARRISYN ® extract as represented by total solid in a unit volume of gel is reduced after acid treatment:

| Sample # | 0 | 1 | 2 | 3 | 4 | 5 | 6 | 7 | 8 |
|---|---|---|---|---|---|---|---|---|---|
| pH | 4.56 | 4.07 | 2.45 | 3.35 | 5.09 | 10.56 | 6.16 | 7.0 | 8.68 |
| Yield % | 0.26 | 0.22 | 0.12 | 0.14 | 0.27 | 0.23 | 0.25 | 0.26 | 0.24 |

However, subsequent aanalyses of the products by infrared spectroscopy and thermogravimetric analysis reveal that the high yield clearly correlated to oxalate and ash content.

Figure 8:
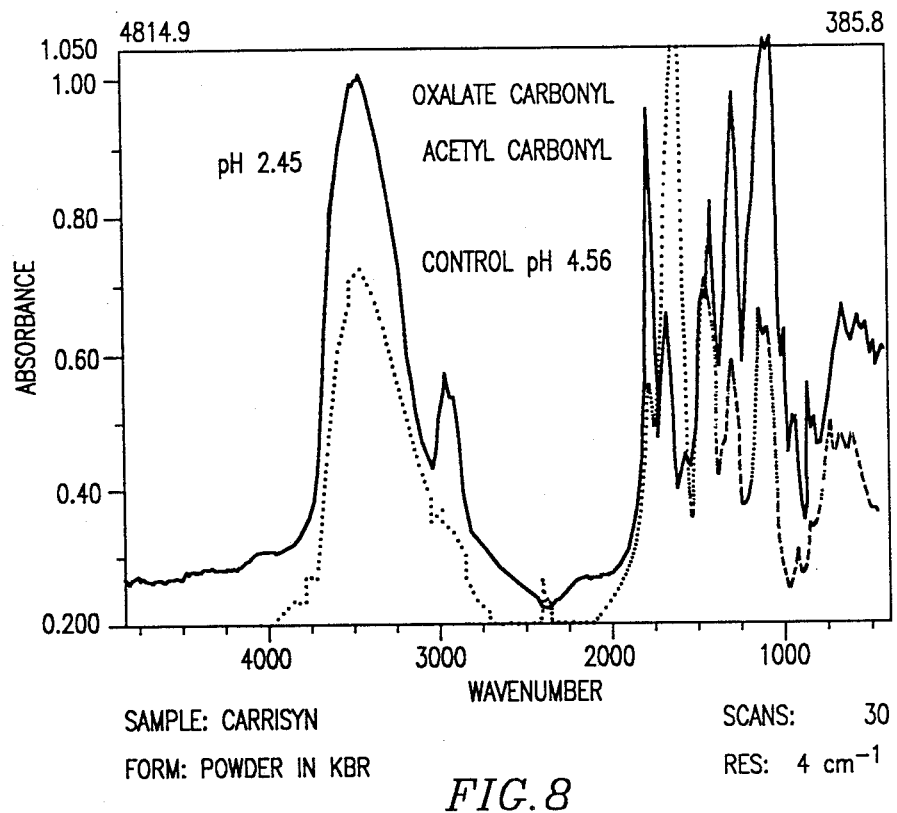
FIG. 8 shows infrared spectra for two samples of CARRISYN ® extract under different pH conditions.

Infrared spectroscopy may be used extensively to characterize CARRISYN ® extract both qualitatively and quantitatively. The increase in the absorption peak of the acetyl group located about 1740 cm$^{-1}$ of CARRISYN ® extract at lower pH demonstrate a reduction of the oxalate content (FIG. 8).

Figure 9:
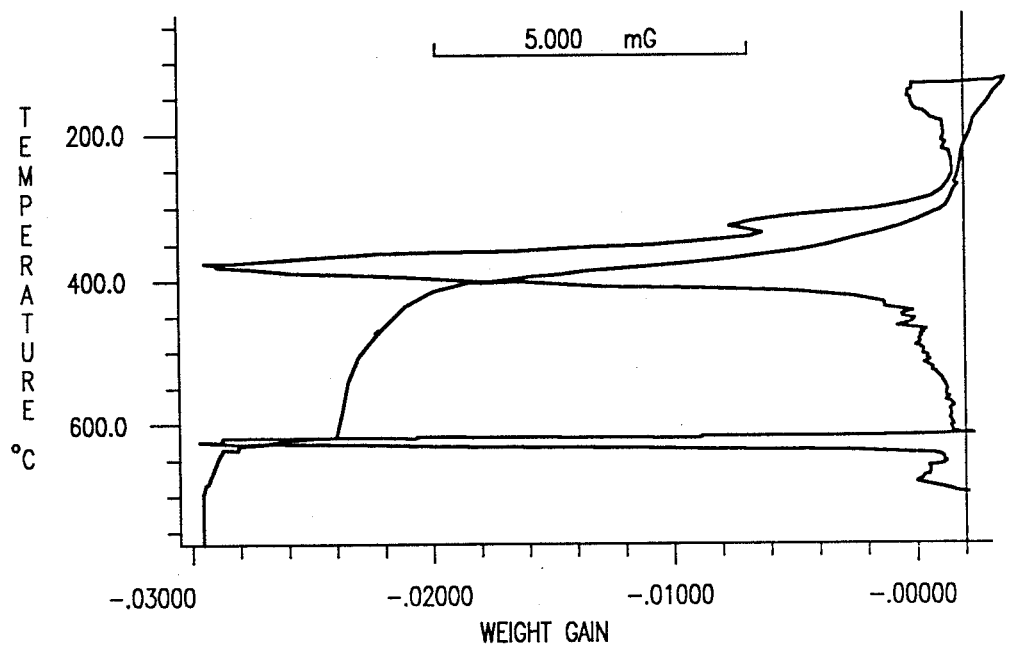
FIG. 9 shows a differential thermogram of CARRISYN ® extract.
Figure 10:
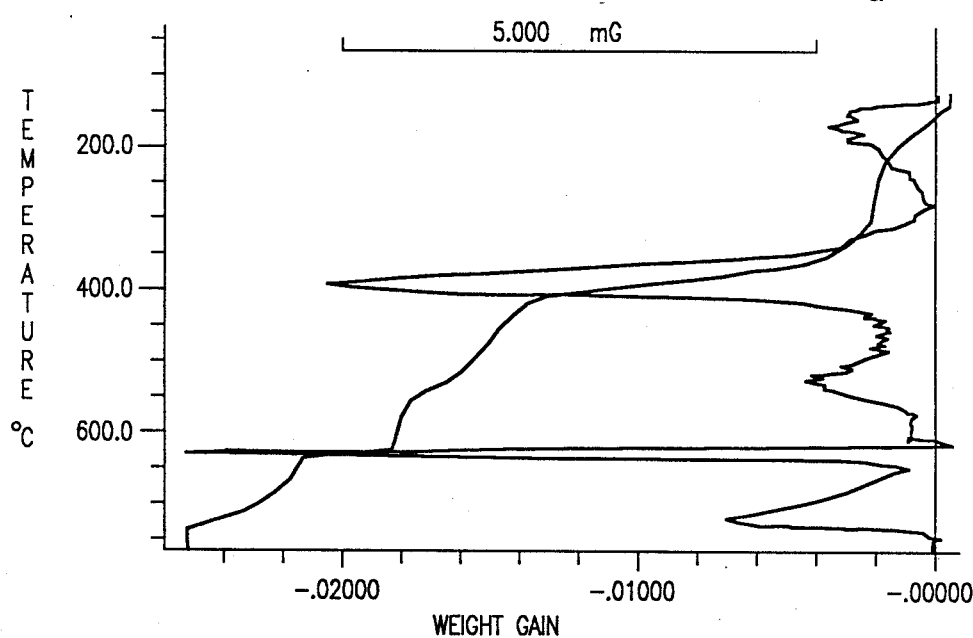
FIG. 10 shows a differential thermogram of CARRISYN ® extract contaminated with calcium oxalate.

Thermogravimetric analysis gives a characteristic weight loss profile with temperature. Generally, pure CARRISYN ® extract gives 3 major peaks on the differential thermogram namely: (a) moisture 30°-100° C., (b) carbohydrate (acemannan) 200°-400° C., and (c) oxidizable carbon skeleton 600°-630° C. (FIG. 9). On the other hand, CARRISYN ® extract contaminated with calcium oxalate, for example, exhibits 2 more peaks located between 456°-500° C. and 650°-720° C. with high ash content (FIG. 10)

Tables 1A-E below present thermogravimetric analyses of CARRISYN ® extract at various pH conditions.

TABLE 1A

THERMOGRAVIMETRIC ANALYSIS OF CARRISYN ® EXTRACT pH 4.56

| SAMPLE ID | WT (mg) | % H$_2$O | % RESIDUE | % CARBOHYDRATE | OXALATE 425 540 C | 631 750 C |
|---|---|---|---|---|---|---|
| 70302 | 9.7220 | 6.9122 | 17.3940 | 49.9485 | 10.3680 | 12.14 |
| 70307 | 8.8020 | 6.6803 | 18.0750 | 51.1364 | 9.7364 | 11.64 |

TABLE 1A-continued

THERMOGRAVIMETRIC ANALYSIS OF CARRISYN ® EXTRACT pH 4.56

| SAMPLE ID | WT (mg) | % H₂O | % RESIDUE | % CARBO-HYDRATE | OXALATE 425 540 C | OXALATE 631 750 C |
|---|---|---|---|---|---|---|
| 70311 | 10.1150 | 6.7721 | 18.9030 | 51.3980 | 8.6604 | 11.36 |
| 70312 | 9.1790 | 6.6347 | 18.4330 | 52.4889 | 8.7700 | 10.89 |
| 70313 | 8.9810 | 5.2667 | 18.5390 | 53.0124 | 8.9522 | 10.85 |
| 70314 | 9.4530 | 4.7287 | 18.5130 | 52.0994 | 9.4785 | 12.19 |
| 70316 | 9.6000 | 5.4271 | 17.7810 | 52.5517 | 9.1771 | 12.19 |
| 70320 | 9.9120 | 5.6094 | 17.0600 | 54.7322 | 8.6259 | 10.62 |
| AVERAGE (X) | 9.4705 | 6.0039 | 18.0873 | 52.1709 | 9.2211 | 11.49 |
| STD DEV N = 8 | 0.4570 | 0.8391 | 0.6325 | 1.4205 | 0.6087 | 0.65 |

TABLE 1B

THERMOGRAVIMETRIC ANALYSIS OF CARRISYN ® EXTRACT pH 3.60

| SAMPLE ID | WT (mg) | % H₂O | % RESIDUE | % CARBO-HYDRATE | OXALATE 425 540 C | OXALATE 631 750 C |
|---|---|---|---|---|---|---|
| 70315 | 9.2100 | 6.9164 | 7.7959 | 72.4104 | 5.6243 | 4.082 |
| 70321 | 10.7180 | 6.5777 | 9.0035 | 70.1716 | 6.4751 | 4.879 |
| 70323 | 9.3070 | 6.0277 | 7.9295 | 73.5680 | 5.1467 | 3.900 |
| 70324 | 9.0919 | 5.2690 | 6.9739 | 74.6780 | 5.0820 | 3.707 |
| 70326 | 9.6950 | 7.0397 | 10.1080 | 70.0355 | 6.4879 | 5.796 |
| 70327 | 9.1490 | 5.7493 | 9.5639 | 69.4942 | 6.6455 | 5.224 |
| 70328 | 9.4680 | 5.5450 | 8.3333 | 68.8317 | 9.5902 | 4.393 |
| 70329 | 9.3140 | 6.4204 | 8.6859 | 71.6130 | 5.5937 | 4.402 |
| AVERAGE (X) | 9.4940 | 6.1939 | 8.5491 | 71.3503 | 6.3307 | 4.548 |
| STD DEV N = 8 | 0.5303 | 0.6478 | 1.0118 | 2.0730 | 1.4527 | 0.708 |

TABLE 1C

THERMOGRAVIMETRIC ANALYSIS OF CARRISYN ® EXTRACT pH 3.20

| SAMPLE ID | WT (mg) | % H₂O | % RESIDUE | % CARBO-HYDRATE | OXALATE 425 540 C | OXALATE 631 750 C |
|---|---|---|---|---|---|---|
| 70330 | 9.3260 | 3.5814 | 6.2621 | 77.1819 | 5.7152 | 3.506 |
| 70331 | 9.8330 | 4.6273 | 4.5764 | 80.7280 | 4.9425 | 1.871 |
| 70334 | 10.8360 | 6.1831 | 5.0388 | 77.6395 | 4.8819 | 2.685 |
| 70401 | 8.1040 | 7.8196 | 4.8618 | 80.3070 | 4.9975 | 2.023 |
| 70402 | 9.0650 | 4.0927 | 4.6222 | 79.4380 | 6.8285 | 1.522 |
| 70403 | 9.9490 | 4.2014 | 4.3220 | 80.1990 | 4.7945 | 2.472 |
| 70405 | 8.8930 | 6.0497 | 4.8353 | 79.1636 | 4.4305 | 2.069 |
| 70406 | 9.8350 | 4.3213 | 4.0874 | 80.9156 | 4.7788 | 1.9420 |
| 70419 | 9.0080 | 5.3619 | 2.1758 | 81.8822 | 4.7069 | 1.7651 |
| 70423 | 9.8510 | 6.6998 | 3.9285 | 79.8803 | 4.7102 | 2.0506 |
| 70426 | 9.7880 | 5.5885 | 4.1479 | 78.8307 | 3.9947 | 1.2873 |
| 70427 | 10.1010 | 6.7815 | 3.2670 | 79.5866 | 4.5144 | 2.0190 |
| 70428 | 10.7790 | 3.6181 | 2.6069 | 80.1190 | 4.4717 | 2.7368 |
| 70431 | 9.9030 | 5.9881 | 4.1099 | 78.4407 | 4.5542 | 2.3831 |
| 70433 | 8.3980 | 6.2277 | 3.5127 | 79.5073 | 4.5844 | 2.2982 |
| 70434 | 9.7360 | 7.1385 | 4.6188 | 77.1878 | 4.5604 | 2.5781 |
| 70440 | 10.0850 | 5.3148 | 3.1730 | 81.4331 | 4.4522 | 1.9534 |
| 70442 | 9.9470 | 6.2933 | 3.3779 | 81.0805 | 4.4234 | 1.2567 |
| 70504 | 9.9740 | 6.2933 | 4.7925 | 77.1410 | 4.7323 | 2.8173 |
| 70505 | 9.1440 | 5.9165 | 3.6308 | 80.5337 | 4.4182 | 1.4545 |
| 70506 | 10.2590 | 5.5659 | 3.4214 | 78.8573 | 5.9460 | 1.9300 |
| 70514 | 10.2060 | 7.7406 | 5.5164 | 74.4461 | 5.2714 | 4.0956 |
| AVERAGE (X) | 9.6827 | 5.7172 | 3.8581 | 79.2956 | 4.8504 | 2.2145 |
| STD DEV N = 22 | 0.6851 | 1.2332 | 1.3386 | 1.7546 | 0.6198 | 0.6831 |

TABLE 1D

THERMOGRAVIMETRIC ANALYSIS
OF RECYCLED CARRISYN ® EXTRACT
20 MINS AGITATION

| SAMPLE ID | WT (mg) | % $H_2O$ | % RESIDUE | % CARBO-HYDRATE | OXALATE 425 540 C | OXALATE 631 750 C |
|---|---|---|---|---|---|---|
| 70515 | 9.8270 | 6.9401 | 9.4739 | 68.5359 | 6.0141 | 6.4109 |
| 70518 | 9.9530 | 5.5059 | 5.3753 | 76.3485 | 5.0638 | 2.9941 |
| 70519 | 10.4880 | 3.4134 | 8.1998 | 68.3159 | 5.9497 | 6.4836 |
| 70523 | 9.5570 | 3.2855 | 6.8013 | 66.6212 | 5.9642 | 7.3663 |
| 70526 | 9.8250 | 5.8321 | 8.1629 | 74.7279 | 4.8651 | 3.1959 |
| AVERAGE (X) | 9.9300 | 4.9954 | 7.6026 | 70.9099 | 5.5714 | 5.2902 |
| STD DEV N = 5 | 0.3437 | 1.5944 | 1.5611 | 4.3276 | 0.5990 | 2.0401 |

TABLE 1E

THERMOGRAVIMETRIC ANALYSIS
OF RECYCLED CARRISYN ® EXTRACT
40 MINS. AGITATION

| SAMPLE ID | WT (mg) | % $H_2O$ | % RESIDUE | % CARBO-HYDRATE | OXALATE 425 540 C | OXALATE 631 750 C |
|---|---|---|---|---|---|---|
| 70528 | 9.6900 | 5.7069 | 6.1197 | 77.7195 | 4.7678 | 2.633 |
| 70529 | 9.2960 | 7.0998 | 4.9699 | 75.8714 | 4.5611 | 3.001 |
| 70535 | 9.7970 | 6.5428 | 4.3483 | 79.3609 | 4.2462 | 1.194 |
| AVERAGE (X) | 9.5943 | 6.4498 | 5.1460 | 77.6506 | 4.5250 | 2.182 |
| STD DEV N = 3 | 0.2638 | 0.7011 | 0.8987 | 1.7457 | 0.2627 | 0.922 |

The tables reveal that:
1. CARRISYN ® manufactured from a starting gel having a pH in excess of 4.56 demonstrated average total carbohydrate and residue (ash) contents of 52.2% and 18.1%, respectively.
2. With adjusted pH of starting gel from about 4.56 to 3.60, the carbohydrate and ash contents were 71.4% and 8.55% respectively. This is an improvement of 36.8% and 52.8% for each measured parameter.
3. However, with a pH of 3.20, the average carbohydrate content jumped to 79.3% while ash content decreased to signifying a carbohydrate increase of about 51.2% and ash decrease of 78.7%.
4. Preliminary data demonstrates that CARRISYN ® extract batches with increased carbohydrate content and lower ash value demonstrated better antiviral activity; it is therefore recommended that processing be conducted at a pH between 3.00 and 3.50.

TABLE 2

Effects of pH on Quality of
CARRISYN ® Extract - (TGA METHOD)

| pH | 2.45 | 3.35 | 4.07 | 4.56 | 5.09 | 6.16 | 7.00 | 8.68 |
|---|---|---|---|---|---|---|---|---|
| Moisture | 5.6762 | 6.2433 | 6.9750 | 8.4035 | 8.5905 | 8.8431 | 8.9819 | 9.7702 |
| Acemannan | 73.925 | 69.930 | 46.929 | 38.651 | 37.649 | 36.796 | 35.593 | 36.316 |
| Carbon Skeleton | 17.812 | 15.455 | 12.840 | 12.846 | 12.969 | 12.508 | 11.485 | 10.769 |
| Calcium | 0.4990 | 4.3160 | 9.7965 | 10.670 | 10.251 | 10.347 | 11.725 | 10.148 |
| Oxalate Ash | 1.9644 | 3.9494 | 13.811 | 15.999 | 16.847 | 17.908 | 17.192 | 17.198 |
| Yield % | 0.12 | 0.14 | 0.22 | 0.26 | 0.27 | 0.25 | 0.26 | 0.24 |

CARRISYN ® extract (total solid) yield calcium oxalate, ash content and moisture appear to increase with increased pH up to 4–5. But acemannan and the corresponding carbon skeleton increase with decreased pH. Therefore, a pH greater than 4.0 is not recommended if ash and calcium oxalate contents must decreased. A yield of CARRISYN ® extract greater than 0.25 must be analyzed for calcium oxalate contamination.

By treating aloe vera gel with a suitable acid, e.g., a dilute mineral acid, preferably hydrochloric acid, to adjust the pH of the gel to between 3.0 to 3.5 followed by ethanol extraction effected a significant reduction in the amount of oxalates. By this step, both calcium oxalate and ash content may be reduced by more than 80%. The treatment also concentrated the amount of the active CARRISYN ® extract without degrading the polymer as demonstrated by the physicochemical analytical methods.

Two batches of CARRISYN ® extract were manufactured as described in Example 1, but with the additional step of acidification to pH 3.6 prior to ethanol precipitation. In Lot #70315, concentrated nitric acid (61 ml) was added to 20 gallons of homogenized aloe vera gel. In Lot #70321, concentrated hydrochloric acid (171 ml) was added to 45 gallons of homogenized aloe vera gel. The yields were 55.6 g (0.07%) and 186.6 g (0.11%), respectively. Chemical analysis by IR and TGA showed both batches to have similar quality and reduced calcium oxalate. The analyses of these two batches are included in Table 1B.

It should become apparent to one skilled in the art that nitric acid can be used solely for acidification, as well as hydrochloric acid or any other suitable acids.

CHARACTERIZATION OF CARRISYN® EXTRACT

Using pharmaceutical screening techniques, a polysaccharide extracted from aloe vera has now been found to be the active chemical substance in aloe vera. This polysaccharide will be hereinafter referred to as acemannan. Acemannan is an ordered linear polymer of substantially acetylated mannose monomers. Other ingredients, such as proteins, organic acids, anthraquinones, vitamins and amino acids make up less than one percent of CARRISYN® extract. The concentration of CARRISYN® extract in aloe vera has been found to be approximately 0.05 to 0.3 weight-percent of the aloe vera juice. The yield or concentration of CARRISYN® extract in the leaves depends on leaf maturity.

The pharmacological data that evidences that acemannan is the active chemical substance in aloe vera and can be summarized as follows:

1. The dose-response of acemannan was the same as Aloe vera juice with an equivalent amount of acemannan.
2. Acemannan was effective in the ulceroprotection model by different routes of administration, namely intravenously, intraperitoneally, and orally.
3. Acemannan accounted for 100 percent of the effects in both pharmacological models.
4. The chemical substance, glucomannan, a substance similar to acemannan from a completely different source, the Konjac plant, provided some pharmacological response.

CARRISYN® extract has been shown in laboratory studies to increase up to 300% in 48 hours the replication of fibroblasts in tissue culture which are known to be responsible for healing burns, ulcers and other wounds of the skin and of the gastrointestinal lining.

CARRISYN® extract has also been shown to increase DNA synthesis in the nucleus of fibroblasts. The increase in DNA synthesis in turn increases the rate of metabolic activity and cell replication which are fundamental steps to the healing process.

CARRISYN® extract has been shown in controlled studies to increase the rate of healing in animals.

CARRISYN® extract has also been shown to be an effective treatment for gastric ulcers in animal studies. Over a three year period, laboratory rats, the stomachs of which react similarly to that of humans, were tested. CARRISYN® extract was found to be equivalent to or superior to current medications used for the treatment of gastric ulcers. Most such products act to inhibit hydrochloric acid in the stomach. CARRISYN® extract works on a different principle and does not alter the natural flow of digestive acids.

As noted above, CARRISYN® extract can be precipitated out of liquidified aloe vera gel by the addition of a water soluble, lower aliphatic polar solvent, preferably ethyl alcohol. CARRISYN® extract powder can then be prepared by lyophilization, and optionally, the lyophilization product can be ground into a powder with a grinding apparatus such as a Moulinex coffee-grinder (available from Dillard's, Dallas, Tex.). CARRISYN® extract powder is highly electrostatic and is an off-white to pinkish-purplish amorphous powder depending on the oxidization state of any anthraquinone contaminant. CARRISYN® extract is stabilized and becomes substantially non-degradable by freeze drying or lyophilization, which removes the water which causes hydrolysis. Freeze dried aloe vera gel with a given amount of CARRISYN® extract has maintained its effectiveness for two years. It is believed that CARRISYN® extract in freeze dried form will be stable for up to ten years.

Heat and time have been found to be important factors in the production of powdered CARRISYN® extract. Heat can aid in the hydrolysis or degradation of CARRISYN® extract, and the longer it takes to process out the CARRISYN® extract at a given temperature, the more is the degradation. Accordingly, it is preferred that the process which allows for the quickest extraction of CARRISYN® extract from whole aloe vera leaves be used when high molecular weight CARRISYN® extract powder is desired, and it is preferred that the process which allows for the slowest extraction of CARRISYN® extract from whole aloe vera leaves be used when low molecular weight CARRISYN® extract powder is desired.

Rehydration of CARRISYN® extract powder at a weight/volume concentration of 0.2 to 1 percent resulted in the reformation of a viscous "gel" like fresh Aloe vera. The gel-like consistency, which returns upon rehydration of CARRISYN® extract powder, is indicative of the high molecular weight polysaccharidic nature of CARRISYN® extract. Generally, as polysaccharides are degraded or hydrolyzed, their viscosity is lowered. Accordingly, the viscosity of rehydrated CARRISYN® extract powder gives a good indication of quality and may be used as a parameter for quality assurance.

CARRISYN® extract, produced according to the process of the present invention, may be characterized as a substantially non-degradable lyophilized ordered linear polymer of acetylated mannose monomers, preferably bonded together by $\beta$ (1→4) bonds.

Various modifications of the disclosed compositions of the invention, as well as alternative modifications, variations and equivalents, will become apparent to persons skilled in the art upon reading the above general description. The following Examples (Examples 5-8) were conducted in order to further characterize and identify CARRISYN® extract. The following examples are illustrative only, and are not intended to limit the scope of the appended claims, which cover any such modifications, equivalents or variations.

EXAMPLE 5

Isolation, Purification And Characterization of CARRISYN® Extract

A. Isolation of CARRISYN® Extract

An aloe leaf was washed, sliced open and filleted. The clean inner gel was retained while the green rind and latex materials were discarded. The filleted material was homogenized and extensively filtered with a Finisher Model 75 (FMC, Chicago, Ill.), to remove most of the pulp. The clear, viscous gel was acidified to a pH of approximately 3.20 with dilute HCl to solubilize the oxalates and lactates of calcium and magnesium that are usually present to their corresponding water soluble acids. The acid treated gel was then extracted for 4-5 hours with four volumes of 95% ethanol at ambient temperature. Floating fibers were removed, then the alcohol/water mixture was siphoned off while the solid precipitate was collected by centrifugation. Most alcohol/water soluble substances such as organic acids, oligosaccharides, monosugars, anthraquinones and inorganic salts were eliminated in the process. The solid was then washed with fresh alcohol, centrifuged, freeze dried, and ground to a white amorphous powder.

B. Purification

Figure 11:
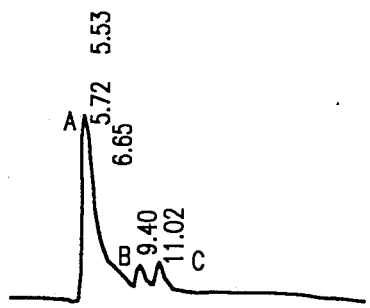
FIG. 11 shows a schematic for the characterization of CARRISYN ® extract.

CARRISYN® extract at this stage is generally contaminated with proteins, monosugars, oligosaccharides and inorganic salts. These contaminants do not affect the bioactivity of the product, hence further purification is not necessary for manufactured bulk material. However, as a further step in the characterization of CARRISYN® extract, more purification steps were added. The above-mentioned contaminants were removed by redissolving the bulk powder in phosphate buffer and treating it with non-specific protease (Sigma Lot #5147) followed by extensive dialysis. The non-filterable product, which is mainly acetylated polymannose, was freeze dried and characterized using a number of analytical methods which include IR spectroscopy, thermogravimetric analysis (TGA), HPLC, GLC and GC/MS as depicted in FIG. 11.

For the standardization of aloe vera products, HPLC and GC are recommended. The gas liquid chromatographic (GLC) method is used to separate and quantitate mannose in aloe vera gel extract. In order to prevent the spiking of products with mannose to make a product appear to have a higher aloe gel content, a dialysis step may be added (MW cutoff 12,000–14,000). In addition, spiking with locust bean gum, guar gum or glucomannan could be detected by high galactose or glucose to mannose ratio.

C. Molecular Weight Determination

Introduction:

Acemannan (AM) is a plant extract polysaccharide. It is polydispersed, which means that it is comprised of more than one molecular weight size.

Objective:

The object of the study is to determine the molecular weight distribution of acemannan by size exclusion chromatography.

Reagents and Chemicals:

0.05% sodium azide.

Standards:

0.2% (w/v) of each standard, Pullulan 853K, 100K and 12.1K daltons in 0.05% sodium azide. (Shodex P-82, Showa Denko, K.K.)

Instrumentation:

High performance Liquid Chromatograph, model 590 (Waters Associates, Milford, Mass.)

Differential refractometer, model 1770 (Bio-rad)

Integrator SP 4290 (Spectra-Physics)

Sample Preparation:

Weigh 20 mg of CARRISYN® extract into a glass vial (105×25 mm) with a teflon lined cap.

Add 10 mL of 0.05% sodium azide and dissolve by shaking (4 hours) in a Junion orbit shaker (Lab-Line Instruments, Mel Rose Park, Ill.).

Filter through a 1.2 um membrane (Acrodisc®, Gelman Sciences). Save the filtrate for an injection into the HPLC.

High Performance Liquid Chromatographic (HPLC) Conditions

Column: Spherogel TSK 5000 PWHR (Beckman Instruments)

Detector: Differential refractometer (Bio-rad)

Mobile Phase: 0.05% sodium azide

Flow rate: 1 mL/min at 40° C.

Vol. inj.: 50 uL

Figure 12:
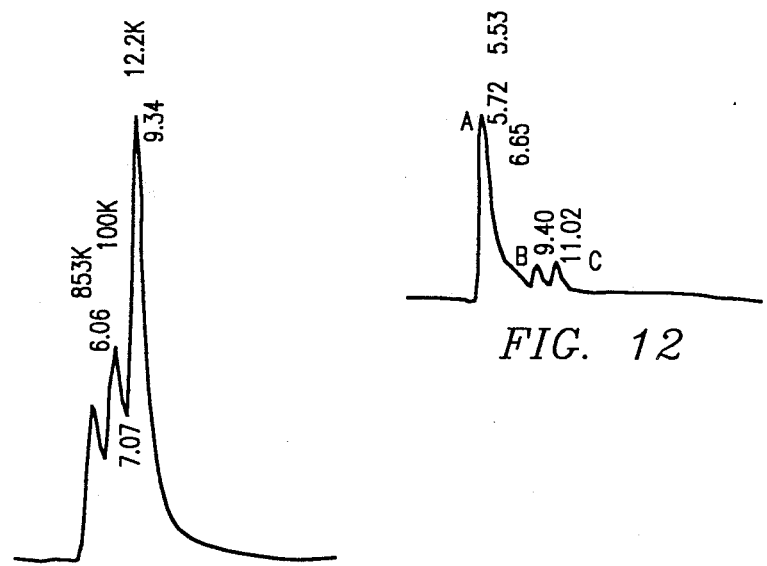
FIG. 12 shows a size exclusion chromatogram of pullulan polysaccharide standards.
Figure 13:
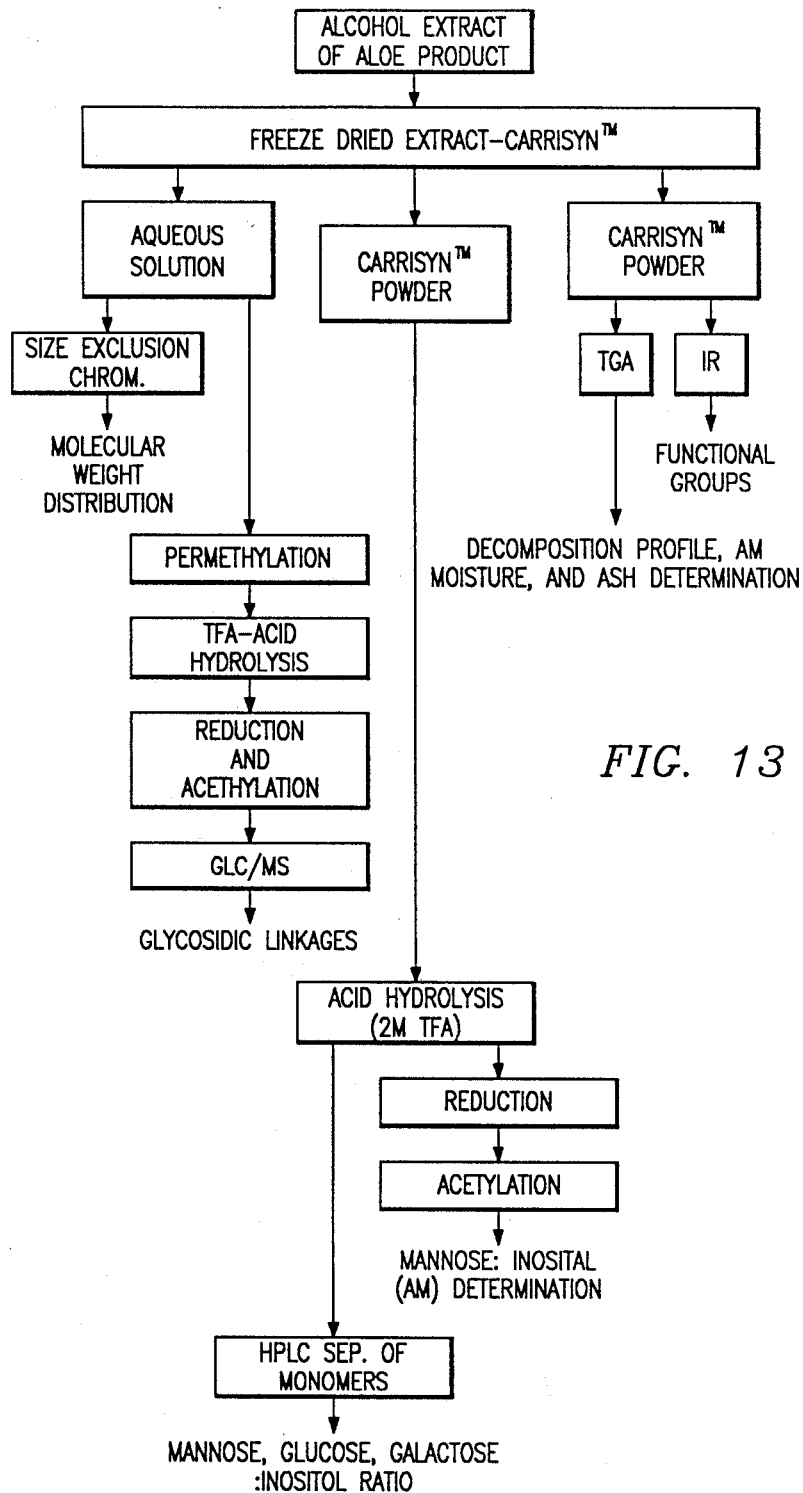
FIG. 13 shows a size exclusion chromatogram of CARRISYN ® extract.

Results:

Acemannan is a polydispersed polysaccharide with at least 73% of the polymer greater than 10,000 daltons as determined by size exclusion chromatography (SEC) and pullulan polysaccharide as the standard. FIG. 12 represents the SEC chromatogram of pullulan standard of known molecular weights; 853K, 100K and 12.1K daltons, respectively. The corresponding chromatogram of CARRISYN® extract is shown in FIG. 13. The chromatogram highlights three (3) main peak fractions, labeled A, B, and C. Peak A represents the acemannan fraction greater than 100,000 daltons and peak B is the fraction greater than 10,000, but less than 100,000 daltons. Peak C represents lower molecular weight constituents. The sum of peaks A and B constitute the active fraction.

D. Infrared (IR) Spectroscopic Analysis

Introduction:

The functional groups of acemannan, the active product of CARRISYN® extract, absorb at characteristic infrared frequencies. Infrared spectroscopy therefore, is an important method to characterize this material.

Objective:

The objective of the study is to further characterize CARRISYN® extract by an infrared spectroscopic method.

Reagents and Chemicals:

Infrared grade potassium bromide (KBr) powder (Mallinckrodt Inc., Paris, Ky.).

Instrumentation:

IBM Fourier Transform infrared (Ft-In) spectrometer model #32 equipped with an IBM 9000 computer and a printer/plotter.

Sample Preparation:

CARRISYN® extract is preground to fine powder by using Wiley Mill (Thomas Scientific Co.) and a screen which allows particles smaller than 60 mesh size.

A 5 mg preground sample is mixed with 495 mg of dry KBr to a total of 500 mg. mixture.

The mixture is reground by hand using agate mortar and pestle to a homogenous material.

A representative sample (80–100 mg) is pressed into a transparent disc using a hydraulic jack (Walker®) at a pressure of 40,000 psi.

The disc is scanned from 4000 $cm^{-1}$ to 400 $cm^{-1}$. A multiple scan (30 scans) is performed with a 4 $cm^{-1}$ resolution to improve signal to noise ratio.

Figure 14:
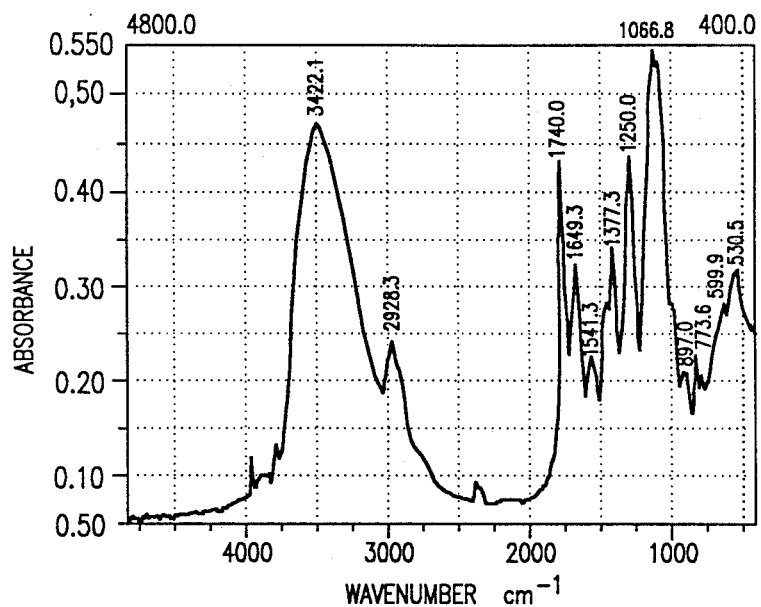
FIG. 14 shows an infrared spectrum of non-protease treated CARRISYN ® extract.

Results:

Analysis of the spectrum depicted in FIG. 14 highlights the following characteristic absorption peak frequencies ($cm^{-1}$):

| Wavenumber ($cm^{-1}$) | Assignment |
|---|---|
| 1066.8 | C—O stretch of pyranose ring structure |
| 3422.1 | 0—H stretch |
| 1250.0 | C—O—C stretch (acetyl group) |
| 1740.0 | C=O stretch (acetyl) |

-continued

| Wavenumber (cm$^{-1}$) | Assignment |
|---|---|
| 1377.3 | C—H bending |
| 1649.3 | C=O stretch (Amide I) |
| 530.5 | Internal rotation modes etc. |
| 599.9 | Internal rotation modes etc. |
| 2928.3 | C—H stretch |
| 1541.3 | N—H deformation (Amide II) |
| 806.3 | — |
| 897.0 | Axial H on ring at C$_1$ |
| 773.6 | ring breathing |

It is noted that the spectrum of CARRISYN® extract demonstrates a strong absorption due to O-H stretching about 3422 cm$^{-1}$. The carbonyl and C-O-C stretches of acetyl group are located near 1740 and 1250 cm$^{-1}$ respectively. The strong single band of C-O-C system is indicative of O-acetyl group bonded equatorially to the monomer unit. The amide carbonyl stretch (amide I) at about 1649 cm$^{-1}$ superimposed on the moisture absorption peak and the N-H deformation (amide II) about 5141 cm$^{-1}$ are due to protein/proteoglycan impurities.

The absorption bands between 960–730 cm$^{-1}$ can be correlated with certain stereochemical features of acemannan. For example, the absence of a band near 844 cm$^{-1}$ due to equatorial C$_1$-H and the presence of axial C$_1$-H near 897 cm$^{-1}$, demonstrate that the acemannan is B-linked. The ring vibration (955 cm$^{-1}$ shoulder) and the ring breathing located about 773 cm$^{-1}$ indicate a D-mannan with beta-glycosidic linkage.

Table 3 below depicts the peak absorption frequencies with corresponding absorbances arranged according to intensity:

TABLE 3
PEAK ABSORBANCE FREQUENCIES FOR NON-PROTEASE TREATED CARRISYN® EXTRACT

| Peak # | Peak | Peak Start | Peak End | Abs |
|---|---|---|---|---|
| 1 | 1066.8 | 1201.8 | 1049.4 | .546 |
| 2 | 3422.1 | 3433.7 | 3410.6 | .474 |
| 3 | 1250.0 | 1348.4 | 1201.8 | .439 |
| 4 | 1740.0 | 1821.0 | 1699.5 | .433 |
| 5 | 1377.3 | 1410.1 | 1350.3 | .343 |
| 6 | 1649.3 | 1697.6 | 1585.7 | .325 |
| 7 | 530.5 | 582.6 | 493.8 | .313 |
| 8 | 599.9 | 634.7 | 586.4 | .282 |
| 9 | 2928.3 | 2995.8 | 2899.4 | .242 |
| 10 | 1541.3 | 1581.8 | 1527.8 | .226 |
| 11 | 806.3 | 835.3 | 789.0 | .224 |
| 12 | 897.0 | 920.2 | 843.0 | .210 |
| 13 | 773.6 | 787.1 | 750.4 | .207 |

E. Infrared Spectroscopy of Protease Treated CARRISYN® Extract

The infrared spectrum of bulk CARRISYN® extract revealed traces of protein or proteoglycan impurities as demonstrated by the presence of amide I and amide II peaks. Further purification of the bulk material with non-specific protease which hydrolyzes the protein or proteoglycan followed by extensive dialysis, eliminated these impurities.

Figure 15:
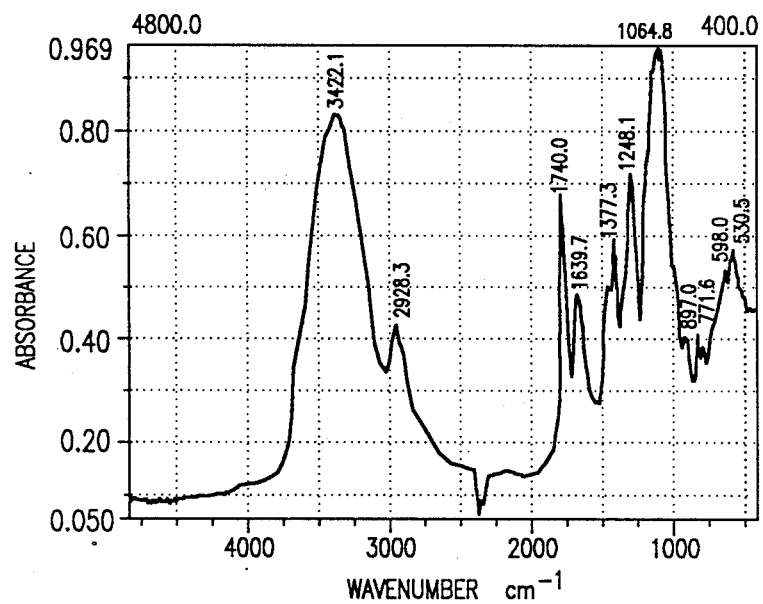
FIG. 15 shows an infrared spectrum of protease treated CARRISYN ® extract.

The spectrum of the protease treated sample is shown in FIG. 15. Analysis of the spectrum shows some differences when compared to the non-protease treated CARRISYN® extract of FIG. 14. For example, the amide I and II peaks located about 1649 and 1541 cm$^{-1}$ in FIG. 14 are absent from the protease treated sample. In addition, the moisture absorption peak located about 1639.7 is clearly resolved. Table 4 represents the peak absorption frequencies with corresponding absorbances arranged according to intensities for protease treated CARRISYN® extract as follows:

TABLE 4
PEAK ABSORBANCE FREQUENCIES FOR PROTEASE TREATED CARRISYN® EXTRACT

| Peak # | Peak | Peak Start | Peak End | Abs |
|---|---|---|---|---|
| 1 | 1064.8 | 1093.8 | 1049.4 | .969 |
| 2 | 1032.0 | 1045.5 | 970.3 | .966 |
| 3 | 3422.1 | 3435.6 | 3404.8 | .814 |
| 4 | 1248.1 | 1348.4 | 1201.8 | .729 |
| 5 | 1740.0 | 1838.4 | 1695.6 | .679 |
| 6 | 1377.3 | 1406.3 | 1350.3 | .593 |
| 7 | 530.5 | 545.9 | 493.8 | .575 |
| 8 | 598.0 | 677.1 | 586.4 | .532 |
| 9 | 1639.7 | 1695.6 | 1554.8 | .491 |
| 10 | 2928.3 | 2990.0 | 2903.2 | .428 |
| 11 | 897.0 | 918.2 | 887.4 | .409 |
| 12 | 806.3 | 835.3 | 790.9 | .409 |
| 113 | 771.6 | 789.0 | 748.5 | .387 |

The absorbance values are not comparable in intensities with the non-protease treated CARRISYN® extract of FIG. 14 since it is qualitative and no attempt was made to use the same concentration in making the sample discs.

On the basis of infrared spectroscopy alone, CARRISYN® extract is a polysaccharide of essentially β-linked D-mannose with O-acetyl group side chains. The presence of N-acetyl groups may be due to protein/proteglycan impurities.

F. Thermogravimetric Analysis (TGA) of CARRISYN® Extract

Introduction:
Thermogravimetric analysis (TGA) is an important analytical method for studying polymers. The mass loss on decomposition of a polymer as a result of temperature change is characteristic of that polymer. Moreover, TGA aids in the determination of moisture (H$_2$O) and ash content of powdered substances.

Objective:
It is the objective of this study to use TGA to further characterize CARRISYN® extract.

Reagents and Chemicals:
None.

Instrumentation:
1. Mettler Thermoanalyzer, TA 3500 system featuring a TC 10A Evaluation and Control computer, as well as a TG 50 furnace wdith M3-03 microbalance.
2. Printer/plotter model MP3 (Print Swiss Matrix).
3. IBM PC for file storage.

Sample Preparation and Analysis:
A 10 mg sample in a 70 mL alumina crucible is weighed in a microbalance accurate to ±1 ug.

The crucible with its contents is heated in the TG 50 furnace at a temperature program rate of 20° C./min. This rate of heating is standard and adequate for the material to be analyzed Heating is performed in a nitrogen gas atomsphere from 25° C. to 60.0° C. and then from 601° C. to 780° C. in air (oxidant) atmosphere.

The temperature is held at this final temperature for an additional two (2) minutes. (The maximum temperature of 780° C. is chosen because both organic and inorganic substances decompose before this temperature is reached).

Figure 16:
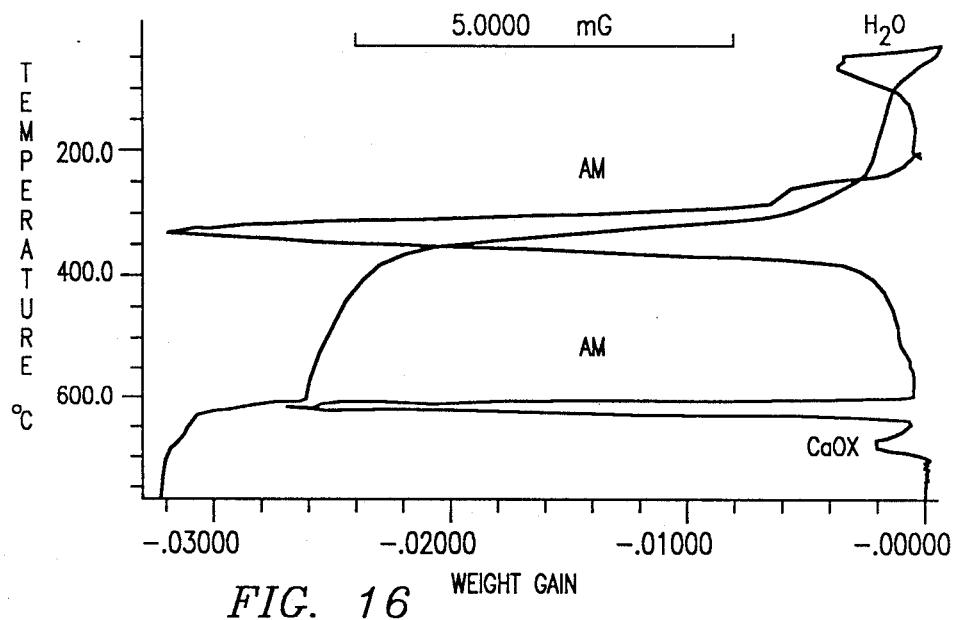
FIG. 16 shows a differential thermogram of CARRISYN ® extract.

Results:

The decomposition profile of CARRISYN ® extract is characteristic. FIG. 16 depicts the real time plot and the corresponding first derivative plot of the decomposition profile of CARRISYN ® extract. The acemannan (the active substance of CARRISYN ® extract) decomposition pattern is different from those of other polysaccharides. For example, under identical operating conditions, the temperature at which acemannan exhibits major decomposition is different from those of cellulose, dextran or amylan. The weight loss associated with acemannan is located between 200° C. and 630° C. The bulk of CARRISYN ® extract's decomposition occurs between 200° C. and 540° C. and 600° C. to 630° C. The acemannan fraction is determined by the contribution of these two temperature regions, while ash and moisture together contribute about 10% by weight. Table 5 below represents a replicate analysis of CARRISYN ® extract with TGA.

TABLE 5

TGA ANALYSIS OF CARRISYN ® EXTRACT

| Sample # | Weight (mg) | $H_2O$ % | Ash* % | AM % | CaOx % |
| --- | --- | --- | --- | --- | --- |
| 1 | 9.4390 | 7.3631 | 3.8034 | 82.2119 | 2.5532 |
| 2 | 9.5860 | 7.3649 | 4.0163 | 81.8381 | 2.7540 |
| 3 | 9.5210 | 7.4992 | 4.2012 | 81.7568 | 2.9514 |
| 4 | 9.4530 | 7.7118 | 4.1786 | 81.2010 | 2.9620 |
| 5 | 9.4090 | 7.7691 | 3.8793 | 81.6072 | 2.9546 |
| 6 | 9.5960 | 6.8674 | 3.9912 | 82.0969 | 3.1576 |
| 7 | 9.4740 | 7.6209 | 4.1904 | 81.6865 | 2.8605 |
| 8 | 9.5730 | 7.3436 | 4.2411 | 81.0719 | 3.3218 |
| 9 | 9.5550 | 7.9435 | 4.1130 | 80.9652 | 3.2444 |
| 10 | 9.5220 | 7.7715 | 4.3373 | 80.8023 | 3.1611 |
| Ave.** (X) | 9.5128 | 7.5255 | 4.0952 | 81.5238 | 2.9920 |
| Std. Dev. | 0.0626 | 0.3087 | 0.1688 | 0.4864 | 0.2353 |

*The ash consists of the oxides of Ca (1.51), Si (0.1), Na (.55), Mg (.37), Fe (.02) and Al (.00).
**Average value will not total 100% because the process does not account for peaks less than 2% of the base peak.

This method of analysis is qualitative as well as semi-quantitative. For example, the percent acemannan may be determined as follows:

$$\text{Percent (\%) AM} = \frac{\text{mg (200–630° C.)} \times 100}{\text{mg (sample)}} \quad 1.$$

$$\text{Percent (\%) AM} = \frac{\text{mg (200–630° C.) sample} \times 100}{\text{mg (200–630° C.) ref. std.}} \quad 2.$$

The moisture and ash contents are important parameters in powdered drug substances. These parameters are easily determined using the Thermogravimetric method.

G. Constituent Sugar Determination of CARRISYN ® Extract By Acid Hydrolysis and High Performance Liquid Chromatography (HPLC)

Introduction:
Polysaccharides are hydrolyzed to their constituent monomers by acid or enzymatic hydrolysis. A 2M trifluoroacetic acid (TFA) is chosen for the hydrolysis because it is strong enough to hydrolyze the glycosdic bonds, but unlike sulfuric acid, it is gentle enough that the monomeric sugar residues are not destroyed.

Objective:
The objective is to determine the monomeric sugar constituents of the acemannan fraction of CARRISYN ® extract.

Reagents and Chemicals:

1. 2M TFA containing 0.5 mg/mL inositol as the internal standard.
2. Isopropanol.

Instrumentation:
1. Hewlett Packard HPLC model 1084B equipped with an autosampler HP79842A and auto injector HP79841A.
2. Bio-rad differential refractometer model 1770.

Sample Preparation:
Weigh accurately 2.0 mg of CARRISYN ® extract on weighing paper and transfer quantitatively to a (13×100 mm) disposable culture tube with a teflon lined cap.

Add one milliliter (mL) of 2M TFA containing 0.5 mg/mL inositol as an internal standard.

Place the tube in a heating block (Hycel Thermal Block) at 120° C. for approximately 1 hour.

Evaporate the hydrolysate mixture to dryness with dry air.

Redisperse the solid in 1 mL of isopropanol and evaporate to dryness with dry air.

Dissolve the solid in 1 mL of deionized water in preparation for injection into the HPLC column.

HPLC Conditions:
Column: Aminex Carbohydrate HPX-87P (Bio-rad Labs., Richmond, Calif.)
Mobile phase: Deionized water at 80° C.
Flow rate: 0.6 mL/min.
Oven temp: 40° C.
Chart speed: 0.2 cm/min.
Detector Refractive index (Bio-rad #1770)
Attn: 2

Figure 17:
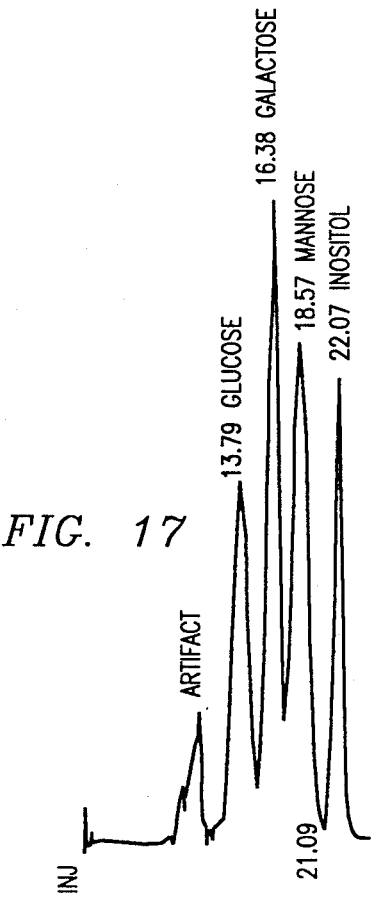
FIG. 17 shows an HPLC chromatogram of a standard mixture of glucose, galactose, mannose and insolitol.
Figure 18:
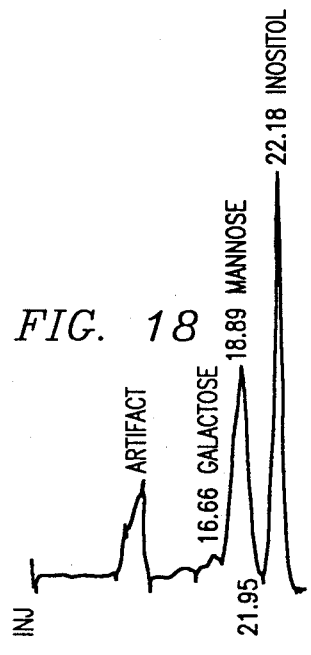
FIG. 18 shows an HPLC chromatogram of CARRISYN ® extract.

Results:
FIG. 17 represents the chromatogram of a standard mixture, comprising glucose, galactose, mannose 1 mg/ml each and 0.5 mg/ml inositol as the internal standard FIG. 18 represents the chromatogram of CARRISYN ® extract under identical conditions. It is noted that mannose is the major component of the polymer signifying that the polysaccharide is essentially composed of mannose sugar units.

H. Gas Liquid Chromatographic Separation and Quantitation of CARRISYN ® Extract

Introduction:
The polysacchride of CARRISYN ® extract is mainly neutral in nature. Neutral polysaccharides are better analyzed by Gas Liquid Chromatography (GLC) as their glycitol acetates.

Objective:
The objective of this study is to further characterize CARRISYN ® extract by separating and quantitating the sugar monomers as their glycitol acetates By this procedure, the glycitol acetates are separated with a capillary column and detected by a flame ionization method.

Reagents and Chemicals:
1. A 2M TFA containing 0.2 mg/mL inositol as the internal standard.
2. Isopropanol
3. 1M $NH_4OH$ containing 10 mg/mL sodium borodeuteride ($NaB^2H_4$) or sodium borohydride ($NaBH_4$)
4. Glacial acetic acid
5. Methanol
6. Pyridine
7. Acetic anhydride
8. Toluene and dichloromethane
9. Gas chromatography (G.C.) grade acetone Instrumentation:
1. Gas chromatograph Vista 6000 (Varian Instrument Group, Palo Alto, Calif.)
2. Integrator SP4290 (Spectra-Physics, San Jose, Calif.)

Sample Preparation:
Weigh accurately 2 mg of sample and transfer into a culture tube (13×100 mm) with a teflon lined cap.

Hydrolysis:
Add 500 uL trifluoroacetic acid TFA-(2M, containing 200 mg/mL inositol), heat at 120° C. (Hycel Thermal Block) for about one hour.

Remove TFA (water bath at 40° C.) under flow of air and wash residue with isopropanol to remove residual acid.

Reduction:
Dissolve residue in 1M NH$_4$OH (300 mL) containing 10 mg/mL sodium borodeuteride (NaB$^2$H$_4$) and leave at room temperature for 1 hour.

Destroy excess reductant with glacial acetic acid (few drops until no effervescence), remove solvents under air and wash residue with methanol containing 10% acetic acid (3×300 uL) and finally methanol (3×30.0 uL).

Acetylation:
To the dry residue add 200 uL pyridine and 200 uL acetic anhyride, heat for 20 min at 12° C.

To the cooled solution add toluene 500 uL, remove solvent under air, dissolve residue in water and extract into dichloromethane.

Transfer the organic phase to a clean tube, remove the organic solvent under air and dissolve residue in acetone (100 uL), prior to GLC.

Gas Liquid Chromatographic Conditions (GLC)

Column: SP 2330, 15M or 30M, 0.25 mm I.D., 0.25 um liquid phase thickness (Supelco, Inc.)
Carrier gas: Helium
Oven temp.: 235° C. (isothermal)
Inj. temp.: 250° C.
Inj. vol.: 0.5–1 uL (split)

Figure 20:
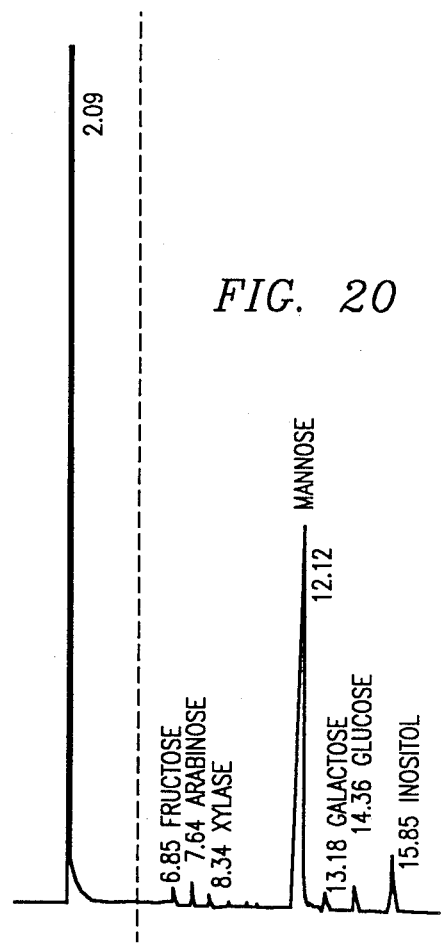
FIG. 20 shows a GLC chromatogram of CARRISYN ® extract.

Results:
FIG. 19 represents the GLC chromatogram of a standard mixture of rhamnose, fucose, arabinose, xylose, mannose, galactose, glucose, and inositol as their glycitol acetates The chromatogram of CARRISYN ® extract is shown in FIG. 20. The major peak in the figure corresponds to mannose. There are traces of galactose, glucose, arabinose, xylose, and fucose. These are from cell wall contaminants. The last peak is inositol acetate which is the internal standard.

Since mannitol acetate is the major sugar peak in the hydrolyzed and acetylated material, CARRISYN ® extract is essentially a polymannose polysaccharide.

Figure 21:
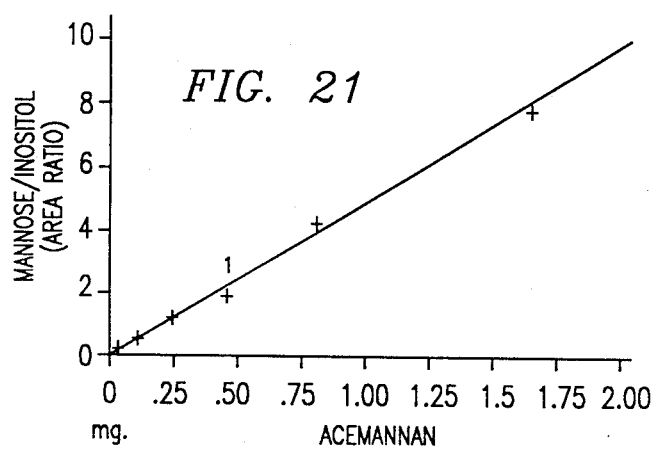
FIG. 21 shows a standard curve of mannose/inositol ratio against amount of acemannan.

The mannitol acetate peak can be quantitated with the help of inositol as the internal standard. FIG. 21 represents a standard curve generated by plotting mannose/inositol area ratio against the known weights of acemannan. With the standard curve, the amount of acemannan in a given sample of CARRISYN ® extract can be calculated.

I. Gas Chromatography/Mass Spectrometry and Glycosidic Linkage Analysis of CARRIYSN ® Extract Introduction:
Polysaccharides are characterized by determining the manner in which the sugar units are linked to one another. The chemical, physical, and biological activities of polysaccharides depend on where the sugars are linked in the five possible positions for the hexoses.

Objective:
It is the purpose of this study to determine the manner in which the sugar units of CARRISYN ® extract polysaccharide are linked.

Reagents and Chemicals:
1. Dry dimethylsulfoxide (DMSO)
2. Sodium dimethylsulphinyl anion (2M)
3. Methyl iodide
4. 2M TFA
5. Isopropanol
6. NH$_4$OH with 50% methanol, 10 mg/mL (NaB$^2$H$_4$)
7. Glacial acetic acid
8. 10% acetic acid in methanol
9. Acetic anhydride
10. Sodium bicarbonate
11. Dichloromethane
12. GC grade acetone Instrumentation:
Gas chromatograph/mass spectrometer MSD (HP 5970).

GLC/MS and Glycosidic Linkage Analysis

Figure 22:
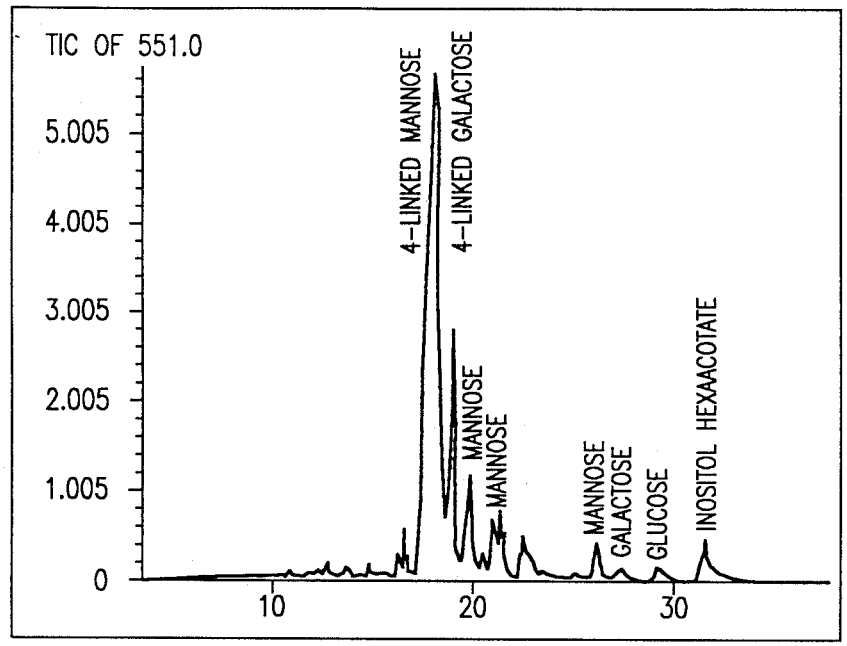
FIG. 22 shows a total ion chromatogram of partially methylated and partially acetylated glycitol of CARRISYN ® extract.

The overall characterization of CARRISYN ® extract includes the linkage analysis of the polymer. CARRISYN ® extract is permethylated by the method described by Darvil et al., (*Plant Physiology*, 62: 418–422 (1978)), the disclosure of which is hereby specifically incorporated herein by reference, hydrolyzed to the monomers and converted to methylated alditol acetates. The volatile derivatives are analyzed on Hewlett-Packard GC/MS system on a Supelco SP 2330 capillary column (30 m×0.25 mm id). Fragmentation of the methylated glycitol acetate of the monomers is achieved by electron impact (EI) method. The total ion chromatogram (TIC) of the derivatized CARRISYN ® as the partially methylated and partially acetylated glycitol is shown in FIG. 22. The mass spectrum of the partially acetylated mannitol is demonstrated in FIG. 23.

The complete procedure is as follows:
(1) The sample (1 mg) is placed in a tube with a teflon lined cap and dried in a vacuum oven at 50° C.
(2) To the sample is added dry DMSO (250 uL) and the sample stirred (teflon stir-bar) until it dissolves (sonication may help). Purge tube with argon (or nitrogen).
(3) To the polysaccharide (in DMSO) is added 250 uL of sodium dimethylsulphinyl anion (2M) and left stirring for a minimum of 4 hours (reaction should be performed under argon). It may be more convenient to leave the sample overnight in the anion solution.
(4) The anion solution is cooled in ice, methyl iodide 200 uL is slowly added and the solution stirred for about 1 hour.
(5) To the solution, add about 2.5 mL water and remove excess methyl iodide with argon.
(6) Transfer the mixture to dialysis tubing, 13.3×2.1 cm in diameter (M.W. cutoff 12,000–14,000, Spectrum Medical, Inc., Los Angeles, Calif.).
(7) Concentrate the non-dialysable fraction under a flow of air (50° C.).
(8) To the dry residue add 250 uL of 2M TFA and heat for 1 hour at 120° C.
(9) TFA under air, wash residue with isopropanol (2×250 uL).

(10) Dissolve residue in aq. NH₄OH 50% methanol (250 uL) containing 10 mg/mL NaB²H₄ leave 1 hour at room temperature.

(11) Destroy excess reductant with glacial acetic acid (few drops), concentrate to dryness and wash residue with 10% acetic acid in methanol (3×250 uL).

(1.2) To the dry residue, add acetic anhydride (100 uL) and heat sample at 120° C. for 3 hours. To the cooled sample add water (about 1.5 mL) and then sodium bicarbonate until effervescence stops. Extract the derivative into dichloromethane.

(13) Concentrate organic phase to dryness, dissolve residue in 100 uL acetone prior to GLC and GL/MS.

GLC Conditions:
Column: SP 2330 fused silica column (30 m×0.25 mm).
Temp.: 3 min at 170° C. followed by 4° C./min to 240° C. hold for 10 min.
Detector FID
GLC/MS conditions:
Column: SP 2330 (30 m×0.25 mm)
Temp.: 2 min at 80° C., increased to 170° C. at 30° C./min then 4°/min to 240° C. hold for 10 min
MS: Hewlett Packard MSD.

Determination of the Major Glycosidic Linkages of Samples by Methylation Analysis In this procedure, all the free hydroxyl groups of the polysaccharide are converted to methyl ethers (step 4). The methylated polysaccharide is hydrolyzed to the constituent monosaccharides (step 8), converted to the methylated alditols (step 9) and acetylated (step 10). These volatile derivatives are analyzed by GLC/MS (step 13) and from the fragmentation patterns, the positions of the O-methyl and O-acetyl groups on the alditols are determined.

Illustration

Figure 25:
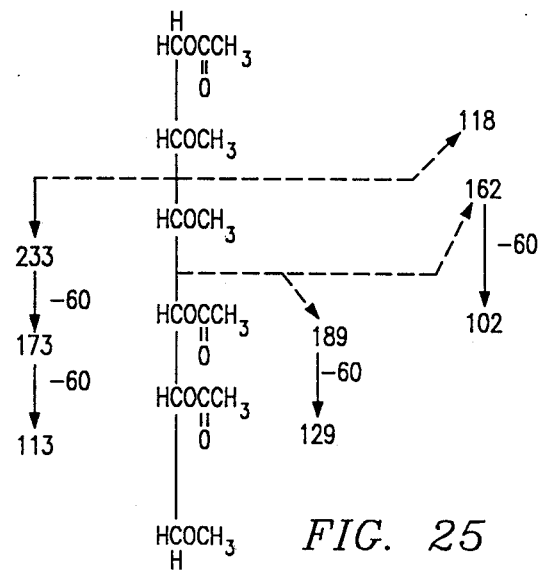
FIG. 25 shows a schematic for fragment ions of methylated mannitol acetate under mass spectrometry analysis.
Figure 23:
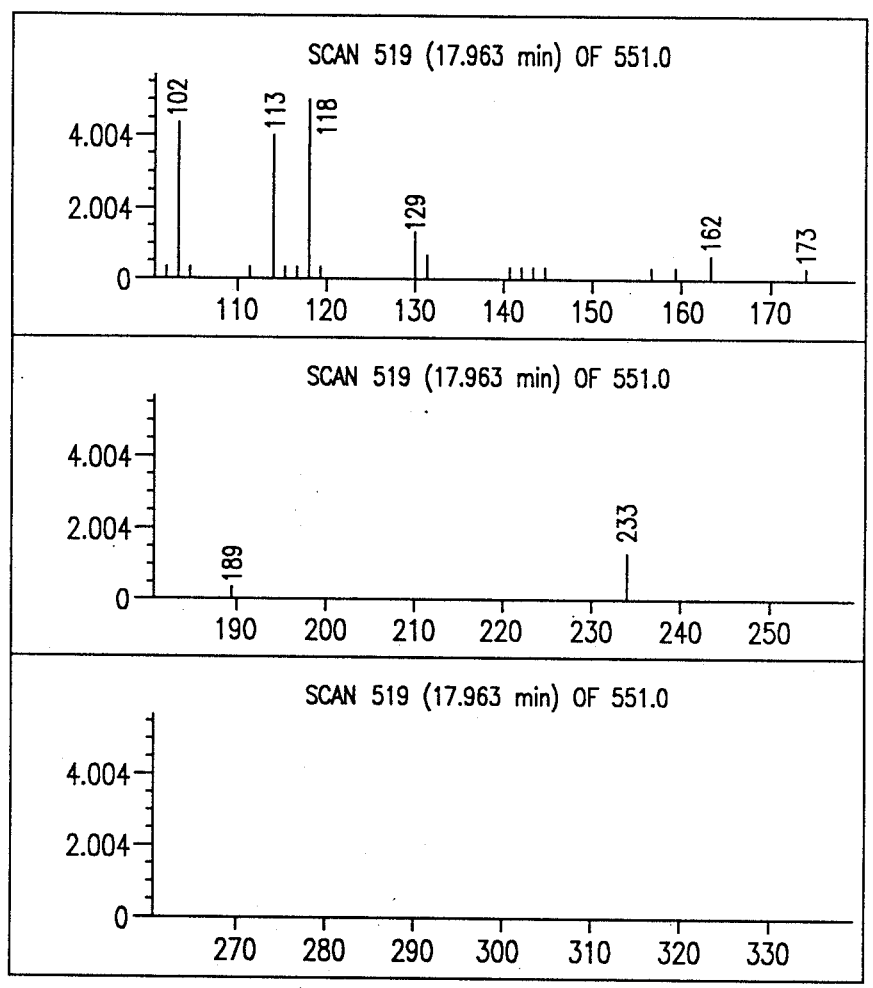
FIG. 23 shows a mass spectrum of the partially acetylated glycitol of CARRISYN ® extract.
Figure 24:
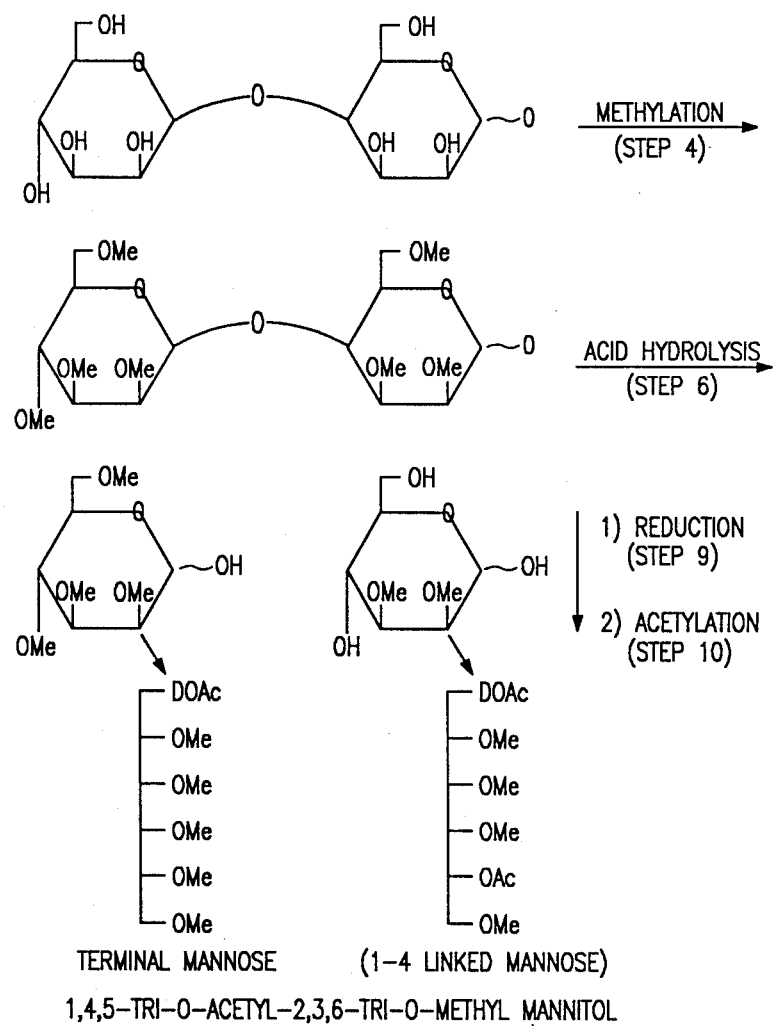
FIG. 24 shows a schematic for partially methylated mannitol acetates.

Consider a glycosyl (mannosyl) residue linked through positions 1 and 4 (i.e. a (1→4-linked mannan). The hydroxyl groups at positions 2, 3 and 6 are free and can be converted to methyl ethers. On hydrolysis and reduction, the hydroxyl groups at positions 1, 4 and 5 are exposed and can be acetylated to yield the derivative 1, 4, 5-tri-O-acetyl-2, 3, 6-tri-O-methylhexitol (FIG. 24). When examined by mass spectrometric technique, the dominant primary fragment ions are produced by cleavage between adjacent O-methyl and O-acetyl groups. The secondary fragment ions are produced by loss of acetic acid, methanol, etc. (FIG. 25). FIGS. 22 and 23 demonstrate the total ion chromatogram of CARRISYN® extract and the mass spectrum of 4-linked mannan as the partially acetylated mannitol respectively.

Based on the total ion chromatogram (TIC) of the CARRISYN® extract and the linakge analysis, it is deduced that CARRISYN® extract is mainly a (1→4)-linked linear polymer of mannose.

EXAMPLE 6

A 32 year old patient was presented with a history of ulcerative colitis for "many years". During an active episode, she had been unresponsive to a daily regimen of 40 mg Prednisone, 3 grams Asulfidine, 50 mg 6-mercaptopurine, and Flagyl. She continued to have a painful abdomen and 4-8 bloody bowel movements per day. She was placed on hyperalimentation. Endoscopic findings revealed severe ascending colon ulcerations with mild hepatic to transverse ulcerations. The patient was placed on 50 mg of CARRISYN® extract q.i.d., in addition to her other medications, and sent home. In one week, her symptoms were virtually gone. The abdomen was mildly tender and endoscopy revealed a healed and mildly congested mucosa. The patient was slowly taken off other medications and the clinical picture continued to improve. The patient is currently maintained on CARRISYN® extract as the sole medication at this time. Physical exam and symptoms are recorded as totally normal.

Five additional cases with similar responses to ulcerative colitis and Crohn's disease have been seen. One patient ran out of CARRISYN® extract capsules. In four weeks, mild symptoms began to recur (there was increased stool with mild abdominal discomfort), and she returned for a supply of medication. In three days she was back to totally normal bowel symptomatology.

EXAMPLE 7

A number of AIDS patients have received prolonged high doses of CARRISYN® extract without toxicity or side-effects. A rise in T-4 and T-8 lymphocyte ratios and an increase in absolute T-4 counts was seen in these AIDS patients with a reduction and elimination of clinical symptoms, as well as a reduction in opportunistic infections. It is suggested that CARRISYN® extract had an anti-viral or immune modulation effect in patients.

A stimulation to the lymphocytes of these patients has been observed which suggests that CARRISYN® extract may be involved in immune modulation.

EXAMPLE 8

The Effect of Alcohol Concentration on CARRISYN® Extract Yield

PROCEDURE:

Hilltop leaves (15.9 lbs.) were washed, filleted and ground in a Waring ™ blender, then filtered through eight layers of cotton cloth. The gel was then transferred to four 11 quart, stainless steel pans, and cold USP grade ethyl alcohol was added to each in two, three, four, and five to one ratios by volume. The amounts can be summarized as follows:

| Ratio (ethanol:aloe gel) | Amt. of Gel | Amt. of Ethyl Alcohol |
| --- | --- | --- |
| 2:1 | 500 ml | 1000 ml |
| 3:1 | 500 ml | 1500 ml |
| 4:1 | 1670 ml | 6680 ml |
| 5:1 | 500 ml | 2500 ml |

The precipitates were allowed to settle out for four hours, then the remaining alcohol-gel solutions were carefully decanted and saved in separate containers. The precipitates were centrifuged for 10 minutes at 2800 rpm using a IEC Centra-7 centrifuge, washed with alcohol, then centrifuged again under the same conditions. The pellets were transferred to 600 ml jars, frozen in liquid nitrogen, and lyophilized overnight.

An additional volume of alcohol was added to the supernatant from the 2:1 ratio and allowed to settle overnight at room temperature. The remaining supernatants were also left at room temperature and allowed to settle out overnight.

The following day, the precipitates were collected from the supernates as previously described, with the exception of the pellet from the 2:1 ratio that had been precipitated with an additional volume of alcohol. In this case, approximately 5–10 ml of water was added as the pellet was transferred to the lyophilization jar.

RESULTS:

The results of the initial, four hour alcohol precipitations can be summarized as follows:

| Ratio (ethanol:aloe gel) | Yield (g) | % Yield (g. CARRISYN ® Extract/g. gel) |
|---|---|---|
| 2:1 | .0518 | .010 |
| 3:1 | .3847 | .077 |
| 4:1 | 1.945 | .116 |
| 5:1 | .6675 | .134 |

After addition of another volume of ethyl alcohol, the 2:1 supernate produced another 178 mg of CARRISYN ® extract. Just by settling overnight, the 3:1 and 4:1 ratio supernates yielded another 89 and 105 mg, respectively. The 5:1 ratio yielded only negligible precipitation after the initial isolation, and was thus not reharvested.

In the case of the second precipitation from the 2:1 ratio (3:1), 5–10 ml of water were used to rinse out the centrifuge bucket before lyophilization. This produced a white, fluffy CARRISYN ® extract of low density that differed greatly from the denser, gray colored CARRISYN ® extract samples that the other samples produced.

SUMMARY

CARRISYN ® extract is a purified white amorphous powder extracted from aloe vera mucilage. The polymer is essentially made up of linear $\beta$-(1→4)-D-mannosyl units. It is a long chain polymer interspersed randomly with acetyl groups linked to the polymer through an oxygen atom. The degree of acetylation is approximately 0.8 acetyl group/monomer as determined by the alkaline hydroxamate method (Hestrin, S.: *J. Biol. Chem.*, 180: 240 (1949)) the disclosure of which is hereby specifically incorporated herein by reference. Neutral sugars linkage analysis indicates that attached to the chain, probably through an $\alpha$ (2–6) linkage, is a D-galactopyranose residue in the ratio of approximately one for every seventy sugars. The ratio of mannose to galactose of 20:1 indicates that galactose units are also linked together, primarily by $\beta$-(1→4) glycosidic bonds.

The chemical structure developed by utilizing modern techniques of polysaccharide characterization is as follows:

```
                        OAc
                         .
                         .
                         2
-B-D-Manp-(1-4)-B-D-Manp-(1-4)-B-D-Manp-(1-4)-B-D-Manp-
    6                              3-6
    .                               .
    .                               .
    .                               .
    2                              OAc
-B-D-galp-(1-4)-B-D-galp-
```

Carrisyn ™ is polydispersed with at least 70% of the material having a molecular weight greater than 10,000 daltons.

Physical and Chemical Properties:

(a) Solubility:

Carrisyn is a white to off-white amorphous powder which dissolves slowly in water to a highly viscous colloidal solution (0.4% w/v). With vigorous shaking for several hours, a 1% (w/v) thick gel may be obtained. Carrisyn is practically insoluble in common organic solvents including propylene glycol. However, Carrisyn dissolves in 20% water and 80% propylene glycol to a smooth thick gel which remains stable indefinitely.

(b) pH:

A 0.2% (w/v) solution of Carrisyn in water has a pH of approximately 6.31±0.33.

(c) Optical Rotation:

The specific rotation of a 0.2% (w/v) aqueous solution of Carrisyn clarified by passing through a 0.45 um membrane filter (Uniflo ™, Schleicher & Scheull Inc., Keene, N.H.) is:

$[\alpha]_{589}^{20} = -20$ signifying a B-linkage. Deionized water was used as the blank.

(d) Alkali Treatment:

Alkal treatment of Carrisyn caused deacetylation which its ability to form a mucilasinous jelly, this indicates that the O-acetylation of CARRISYN ® extract influences its viscosity. The product of deacetylation does not dissolve in water apparently die to increased strong hydrogen bonding.

(e) Infrared Spectroscopy:

The functional groups in CARRISYN ® extract are identified by infrared spectroscopy (FIGS. 14 and 15). The strong IR absorption bands near 1740 cm$^{-1}$ and 1250 cm$^{-1}$ signify acetylation. Other absorptions located about 3422 cm$^{-1}$, 1066 cm$^{-1}$, 1639 cm$^{-1}$, 897 cm$^{-1}$, 806 cm$^{-1}$ and 773 cm$^{-1}$ are characteristic of polysaccharides with $\beta$-mannosyl linkages. Weak amide I and amide II absorptions are located about 1649 cm$^{-1}$ and 1541 cm$^{-1}$ and 1541 cm$^{-1}$ respectively, (FIG. 14) these are due to protein impurities since when the CARRISYN ® extract is treated with protease and dialyzed, these peaks are absent (FIG. 15).

(f) Molecular Weight Distribution:

CARRISYN ® extract is polydispersed with at least 73% of the material greater than 10,000 daltons as determined by size exclusion chromatography. An example of a high pressure liquid chromatogram (FIG. 13) demonstrates three fractions labeled A, B and C. Peak A represents CARRISYN ® extract greater than 100,000 daltons and peak B represents CARRISYN ® extract greater than 10,000 daltons, but less than 100,000 daltons. Peak C represents the molecular weight constituents of CARRISYN ® extract. The area of peaks B and C increase as CARRISYN ® extract decomposes, which, in turn, causes a decrease in the area of Peak A.

It will be readily apparent to those in the art from the broad teaching of the invention and the illustrative examples that there is the possibility of the substitution of unnamed chemicals and steps for the preferred enumerated chemicals and process steps; the lack of mention of such unnamed chemicals and steps does not indicate that they are not within the scope of the invention; but are omitted only because of the requirement that this teaching be concise and exact.

What is claimed is:

1. Process for extracting from the aloe plant a substantially non-degradable lypholized polymer of linear $\beta$ (1→4)-D-mannosyl units wherein randomly interspersed acetyl groups are linked to the polymer through an oxygen atom and wherein D-galactopyranose is linked to the polymer through an α (2-6) linkage at a ratio of about one D-galactopyranose residue per seventy monomer units, comprising:

(a) washing an aloe leaf in a bacteriacidal solution to remove substantially all surface dirt and bacteria;
(b) removing at lest a first end portion from said washed leaf;
(c) removing rind and any remaining anthraquinone-rich sap from said leaf to produce a substantially anthraquinone-free aloe gel fillet;
(d) grinding and homogenizing said substantially anthraquinone-free aloe gel to produce substantially anthraquinone-free aloe juice having solubilized matter;
(e) filtering said ground and homogenized aloe juice to remove fibrous material;
(f) adjusting the pH of said aloe juice of from about 3.00 to about 3.50;
(g) adding a water-soluble, lower aliphatic polar solvent to the aloe juice to precipitate the active chemical substance and thereby to form a heterogeneous solution containing soluble contaminants;
(h) removing the water soluble, lower aliphatic polar solvent and the solubilized matter from the heterogeneous solution to isolate the precipitated active chemical substance; and
(i) drying the precipitated active chemical substance.

2. The process of claim 1 wherein both a first end portion and a second end portion are removed from the washed leaf.

3. The process of claim 2 wherein after the leaf is cut at both ends, and a athraquinone-rich yellow sap is drained, preserved and collected.

4. The process of claim 1 wherein the bacteriacidal solution comprises calcium hypochlorite.

5. The process of claim 1 wherein the water-soluble lower aliphatic polar solvent is an aqueous solution containing ethanol.

6. The process of claim 5 wherein the solvent is about 95% by weight ethanol and about 5% water.

7. The process of claim 1 wherein drying is accomplished by lypholization.

8. The process of claim 1 wherein the water-soluble, lower aliphatic polar solvent and soluble contaminants are removed by a step selected from the group consisting of decantation and centrifugation.

9. Composition of matter, comprising:
a substantially non-degradable lypholized polymer of linear β (1-4)-D-mannosyl units wherein randomly interspersed acetyl groups are linked to the polymer through an oxygen atom and wherein D-galactopyranose is linked to the polymer through an α (2-6) linkage at a ratio of about one D-galactopyranose residue per seventy monomer units, the composition is polydispersed with at least 70% of the polymers having a molecular weight greater than 10,000 daltons.

10. Composition of matter according to claim 9, wherein the degree of acetylation is about 0.8 acetyl groups per monomer.

11. Composition of matter, comprising:
a substantially non-degradable lypholized linear polymer having a repeating monomer comprising:

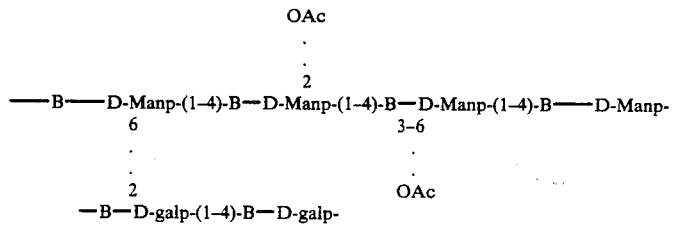

wherein the degree of acetylation is 0.8 acetyl groups per polymer monomer; wherein the galactopyranose units are attached to the polymer at a ratio of approximately one per seventy monomer units; and wherein the mannose to galactose ratio is approximately 20:1.

* * * * *